US009451785B2

(12) United States Patent
Berry et al.

(10) Patent No.: US 9,451,785 B2
(45) Date of Patent: Sep. 27, 2016

(54) COMPOSITIONS FOR DIETARY HEALTH MANAGEMENT

(75) Inventors: Mark John Berry, Sharnbrook (GB); Heather Frances Jennifer Bligh, Sharnbrook (GB); John Casey, Sharnbrook (GB); Karl John Hunter, Sharnbrook (GB); Robèr Antoine Kemperman, Vlaardingen (NL)

(73) Assignee: Conopco Inc., Englewood Cliffs, NJ (US)

( * ) Notice: Subject to any disclaimer, the term of this patent is extended or adjusted under 35 U.S.C. 154(b) by 0 days.

(21) Appl. No.: 13/698,685

(22) PCT Filed: May 25, 2011

(86) PCT No.: PCT/EP2011/058537
§ 371 (c)(1),
(2), (4) Date: Nov. 19, 2012

(87) PCT Pub. No.: WO2011/147862
PCT Pub. Date: Dec. 1, 2011

(65) Prior Publication Data
US 2014/0057843 A1 Feb. 27, 2014

(30) Foreign Application Priority Data

May 28, 2010 (EP) .................... 10164261

(51) Int. Cl.
*A23L 1/29* (2006.01)
*A61K 38/16* (2006.01)
*A23L 1/30* (2006.01)
*A23L 1/308* (2006.01)

(52) U.S. Cl.
CPC ............. *A23L 1/296* (2013.01); *A23L 1/29* (2013.01); *A23L 1/293* (2013.01); *A23L 1/3002* (2013.01); *A23L 1/308* (2013.01); *A61K 38/16* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,352,712 B1 | 3/2002 | Lukaczer et al. |
| 6,808,727 B2 | 10/2004 | Kemeny |
| 2003/0206982 A1 | 11/2003 | Spors et al. |
| 2008/0031925 A1 | 2/2008 | Gannon et al. |

FOREIGN PATENT DOCUMENTS

| | | |
|---|---|---|
| CN | 101305802 | 11/2008 |
| JP | 2004242586 | 9/2004 |
| WO | WO9639050 | 12/1996 |
| WO | WO9639051 | 12/1996 |
| WO | WO9639052 | 12/1996 |
| WO | WO0211562 | 2/2002 |
| WO | WO0211562 A2 | 2/2002 |

OTHER PUBLICATIONS

Cordain. JANA. 5(3):2002.*
Refsgaard et al. J Agric Food Chem. 46:1998.*
Haytowitz et al. Nutrient Data Laboratory, USDA. 2013.*
Turkmen et al. Food Chem 93:2005.*
Luthria et al. J Food Comp Anal. 19;771-777:2006.*
Bastin et al. Cooperative Extension Service, University of Kentucky, College of Agriculture. 1997.*
Aflaki, Neda. Optimization of carotenoid extraction in peel and flesh of cantaloupe (*Cucumis melo* I.), with ethanol solvent. 2012.*
Folin-Ciocalteu reagent, Wikipedia, May 20, 2011, 1-2.
Chamkha et al, Phenolic Composition of Champagnes from Chardonnay and Pinot Noir vintages, Journal of Agricultural and Food Chemistry, Dec. 4, 2003, 51, 3179-3184.
Dillard et al, Review Phytochemicals: nutraceuticals and human health, Journal of the Sicence of Food and Agriculture, May 30, 2000, 80, 1744-1756.
Doka et al, Determination of total polyphenolic content in red wines by means of the combined He—Ne laser optomthermal window and folin-ciocalteu colourimetry assay, Analytical Chemistry, 2002, 74, 2157-2161.
Eaton, Paleolithic Nutrition. A considereation of its Nature and current implications, The New England Journal of Medicine, 1985, 312, 283-389.
Frassetto et al, Metabolic and physiologic improvements from consuming a paleolithic, hunter-gatherer type diet, European Journal of Clinical Nutrition, 2009, 63, 947-955.
Frayling et al., A Common Variant in the FTO Gene is Associated with Body Mass Index and Predisposes to Childhood and Adult Obesity, Science, May 11, 2007, 316(5826)889-894.

(Continued)

*Primary Examiner* — Amber D Steele
*Assistant Examiner* — Schuyler Milton
(74) *Attorney, Agent, or Firm* — Greenberg Traurig, LLP

(57) ABSTRACT

This invention relates to a plurality of compositions for dietary health management and its use in the prevention or treatment of any one of the disease states in the group consisting of cardiovascular disease, inflammation and diarrhoea. Human evolution has been a very slow process in contrast to the relatively recent, rapid changes in our diet since the Neolithic revolution which marked the switch from hunter-gatherer to agricultural life-style around 10,000 years ago. Moreover our genome has not had time to evolve at the same pace and therefore it is postulated that our bodies will work more efficiently with an ancestral diet. In a first aspect of the invention, a plurality of compositions for the dietary health management system of a human being is provided, wherein the plurality of compositions comprise a daily diet of: (g) 1750 to 2750 kilocalories (7350 to 11550 kiloJoules); (h) have more than 1250, preferably more than 1450, more preferably more than 1650 mg gallic acid equivalents of polyphenols; (i) have more than 40, preferably more than 50, more preferably more than 60 g fiber; (j) have more than 130, preferably more than 150, more preferably more than 170 g protein (k) have 0 to 2, preferably 0 to 1.5, most preferably 0 to 1 g starch; and (l) have 0 to 5, preferably 0 to 2.5, most preferably 0 to 1 g lactose.

4 Claims, 9 Drawing Sheets

(56) References Cited

OTHER PUBLICATIONS

Figure 2B:
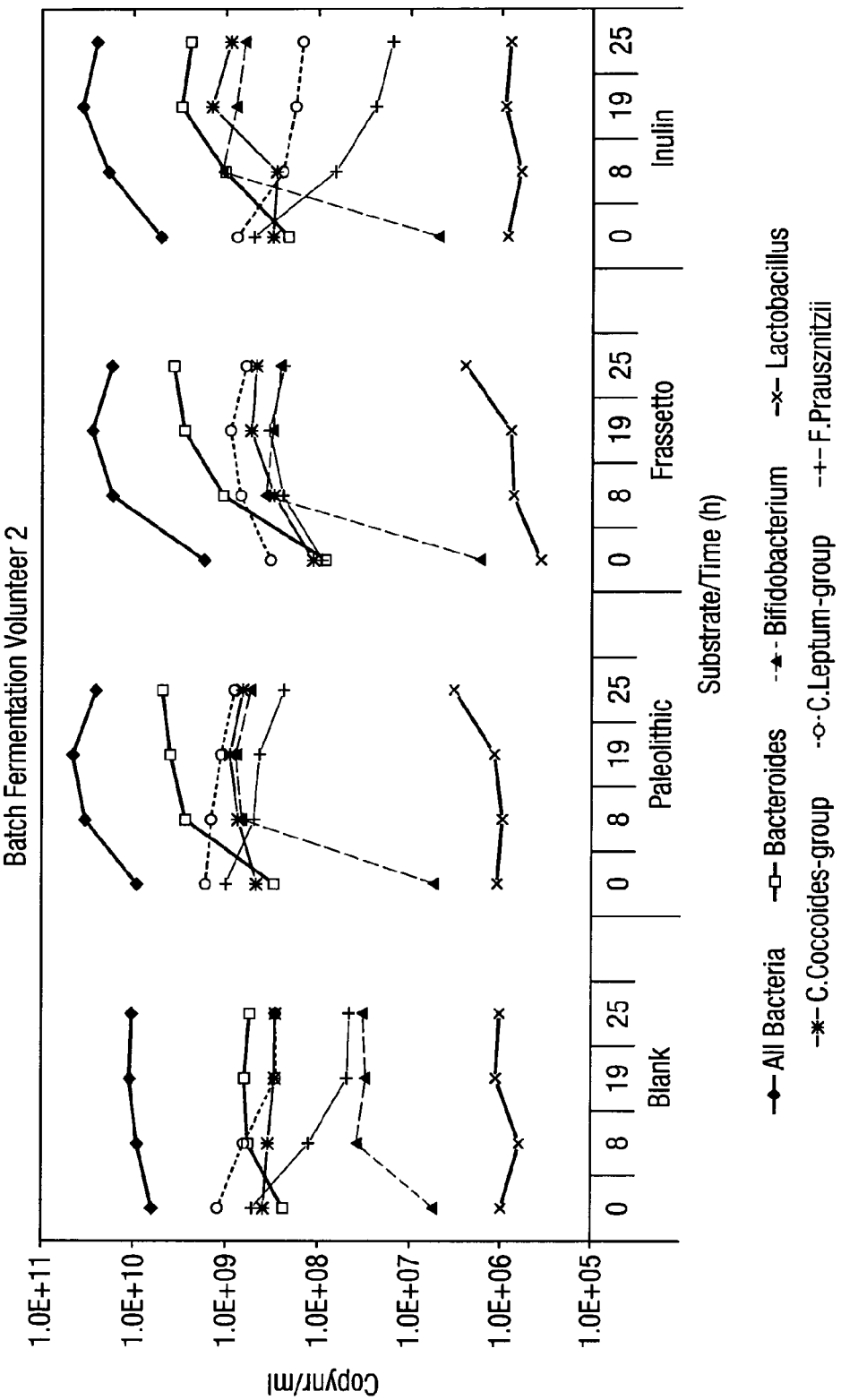

Jew et al, Evolution of the human Diet: linking our ancestral diet to meodern functional foods as a means of chronic disease prevention, Journal of medicinal Food, Jan. 27, 2009, 12, 925-934.

Jonsson et al, Beneficial effects of a paleolithic diet on cardiovascular risk factors in type 2 diabetes: a randomized cross-over pilot study, Cardiovascular Diabetology, Jul. 16, 2009, 8, 1-14.

Koebnick et al., Long-Term Consumption of a Raw Food Diet is Associated with Favorable Serum LDL Cholesterol and Triglycerides but Also with Elevated Plasma Homocysteine and Low Serum HDL Cholesterol in Humans, The Journal of Nutrition, Jul. 23, 2005, 2372-2378, American Society for Nutrition.

Laden et al., The rise of the hominids as an adaptive shift in fallback foods: Plant underground storage organs (USOs) and australopith origins, Journal of Human Evolution, May 7, 2005, 49, 482-498, Elsevier Ltd.

Lindeberg et al, A palaeolithic diet improves glucose tolerance more than a Mediterranean-like diet in individuals with ischaemic heart disease, Diabetologia, Jun. 22, 2007, 50, 1795-1807.

Lopez et al, Analysis of phenolic constituents of biological interest in red wines by high-performance liquid chromatography, Journal of Chromatography A, Apr. 24, 2001, 922, 359-363.

Lu B-Y et al, Foaming and emulsifying properties of pea albumin fractions and partial characterisation of surface-active components, J Sci Food Agric 80, 2000, 80, 1964-1972.

Miller et al, An in vitro method for estimation of iron availability from meals, The Americal Journal of Clinical Nutrition, Oct. 1981, 34, 2248-2256.

Neel, Diabetes Mellitus: A "Thrifty" Genotype Rendered Detrimental by "Progress"?, Am. J. Human Genetics, 1962, 14, 353-362.

Walle et al, Flavonoid glucosides are hydrolyzed adn thus activated in the oral cavity in humans, The Journal of Nutrition, Sep. 30, 2004, 48-52.

Wolfe et al, Apple peels as a value added-food ingredient, Journal of Agricultural and Food Chemistry, Feb. 19, 2003, 51, 1676-1683.

Cohen, Health and the Rise of Civilization, 1989, Yale University Press, 6 pp.

Larsen, Skeletons in our Closet, Revealing our Past through Bioarchaeology, Princeton University Press, 2002, 84-87.

International Search Report for International Application No. PCT/EP2011/058537 with Written Opinion dated Aug. 25, 2011.

Cohen, The Evidence of Prehistoric Skeletons, Health and the Rise of Civilization, 1989, 112-115 & 208-209, Chpt 7, Yale University Press.

Larsen, From Foraging to farming: A Regional Perspective, Skeletons in Our Closet: Revealing our Past through Bioarchaelology, 2002, 84-87, Chapter 3.

Miquel el al, Faecalibacterium prausnitzii and human intestinal health, Current Opinion in Microbiology, Jul. 3, 2013, 255-261, 16.

Everard et al, Cross-talk between Akkermansia muciniphila and intestinal epthelium controls diet-induced obesity, PNAS, May 28, 2013, 9066-9071, vol. 110 No. 22, BE.

Gravitz, The critters within Outlook Diabetes, May 17, 2012, S12-S13, 485 MK.

USDA Nutrition Data Base for Steamed Broccoli.

Bahorun et al., Total Phenol, Flavonoid, Proanthocyanidin and Vitamin C Levels and Antioxidant Activities of Mauritian Vegetables, Journal of the Science of Food and Agriculture, 2004, 1553-1561, 84, ., ., US.

Chassy et al., Three-Year Comparison of the Content of Antioxidant Microconstituents and Several Quality Characteristics in Organic and Conventionally Managed Tomatoes and Bell Peppers, Journal of Agricultural and Food Chemistry, 2006, 8244-8252, 54, ., ., US.

Chun et al., Daily Consumption of Phenolics and Total Antioxidant Capacity from Fruit and Vegetables in the American Diet, Journal of the Science of Food and Agriculture 2005, vol. 85 pp. 1715-1724, 2005, 1715-1724, 85, ., ., US.

Gitanjali P. Yaosda Devi and M. Shiva Prakash, Effect of Shallow Frying on Total Phenolic Content and Antioxidant Activity in Selected Vegetables, Journal Food Science Technology, 2004, pp. 666-668, 41, 6, US.

Wu et al., Lipophilic and Hydrophilic Antioxidant Capacitites of Common Foods in the United States, J. Agric. Food Chem, 2004, 4026-4037, 52, ., ., US.

Mark Houston, Vitamins help Support Children's Health, The Journal of the American Nutraceutical Association, 2002, No. 3, 5.

Stanley Boyd Eaton, Paleolithic vs. modern diets—selected pathophysiological implications, Eur J Nutr 39 67-70 (2000), 67-70, 39.

Jonsson et al, A paleolithic diet is more satiating per calorie than a mediterranean-like diet in individuals with ischemic heart disease, Nutrition and Metabolism, Nov. 30, 2010, 85 (1-14), 7, SE.

SB Eaton, Paleolithic nutrition revisited: A twelve-year retrospective on its nature and implications, European Journal of Clinical Nutrition (1997) 51,207-216, 207-216, 51.

\* cited by examiner

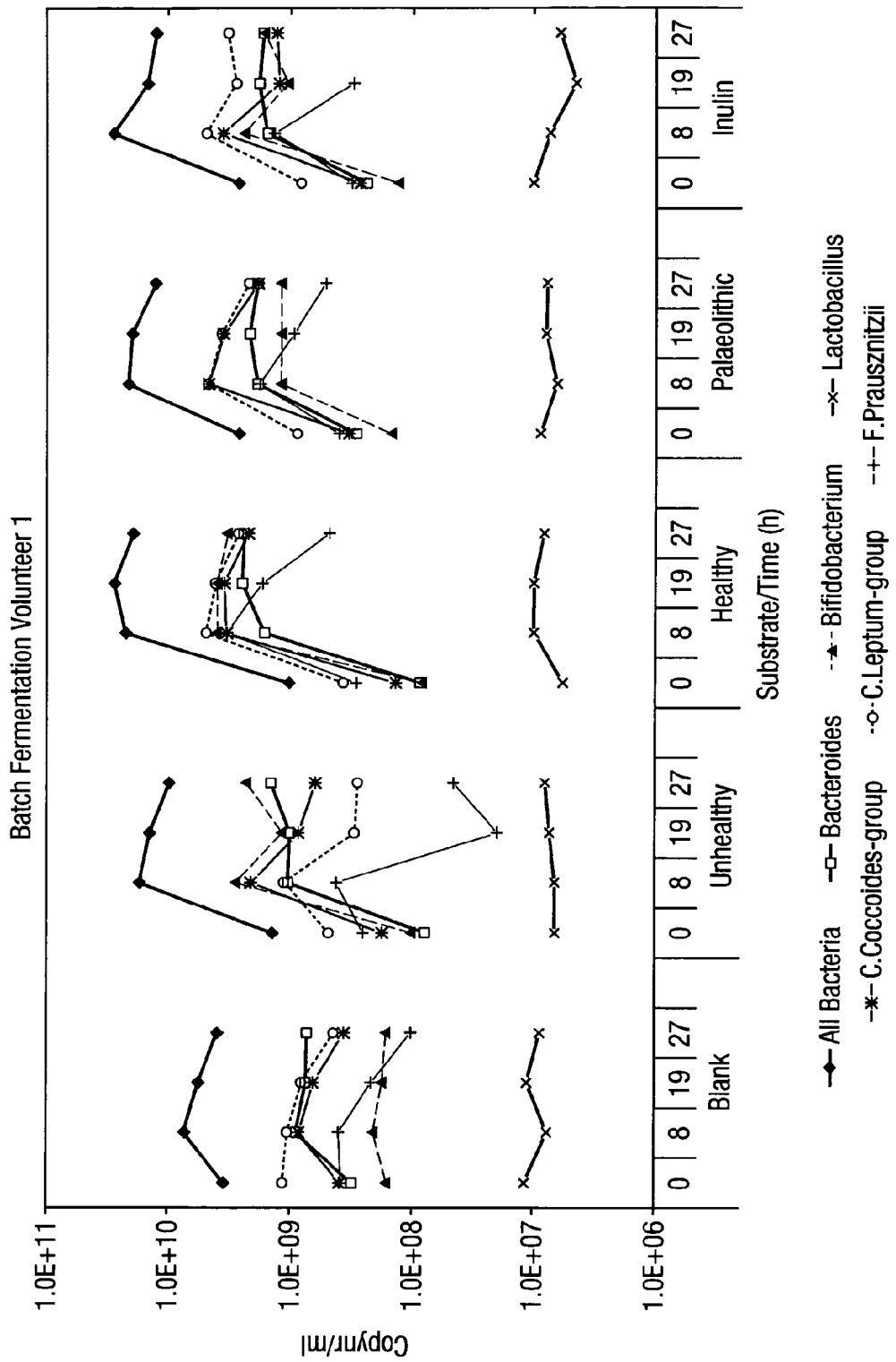

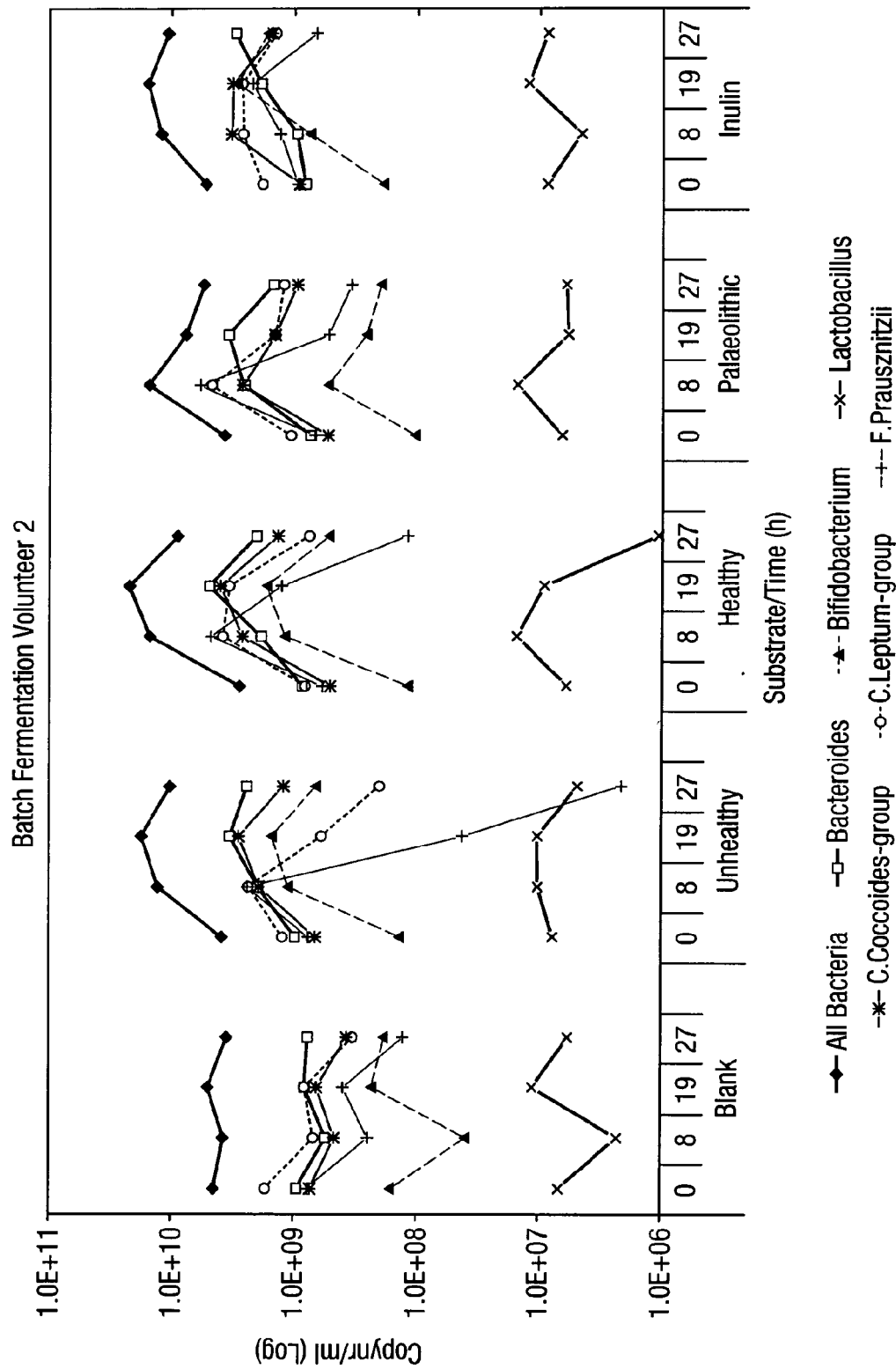

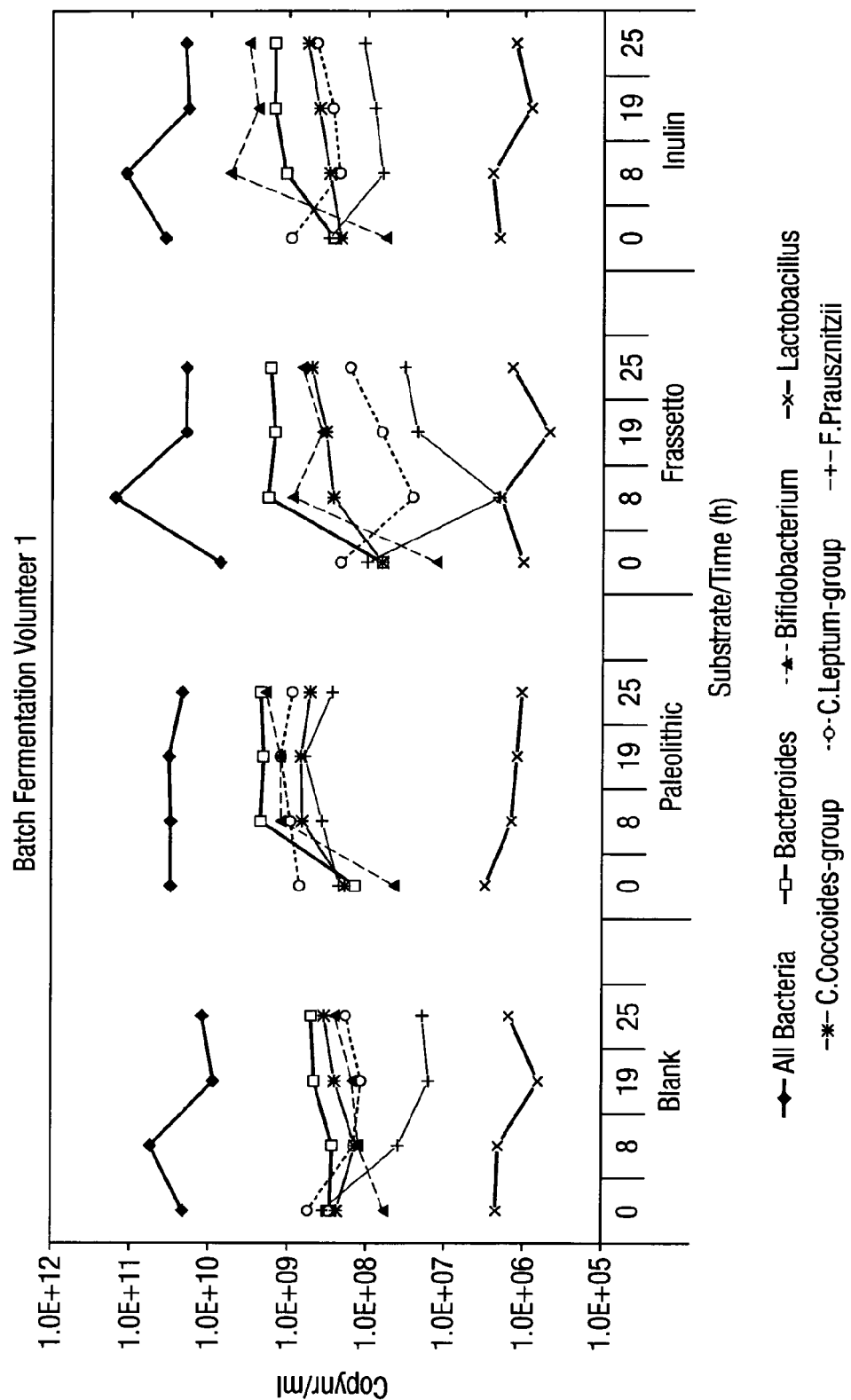

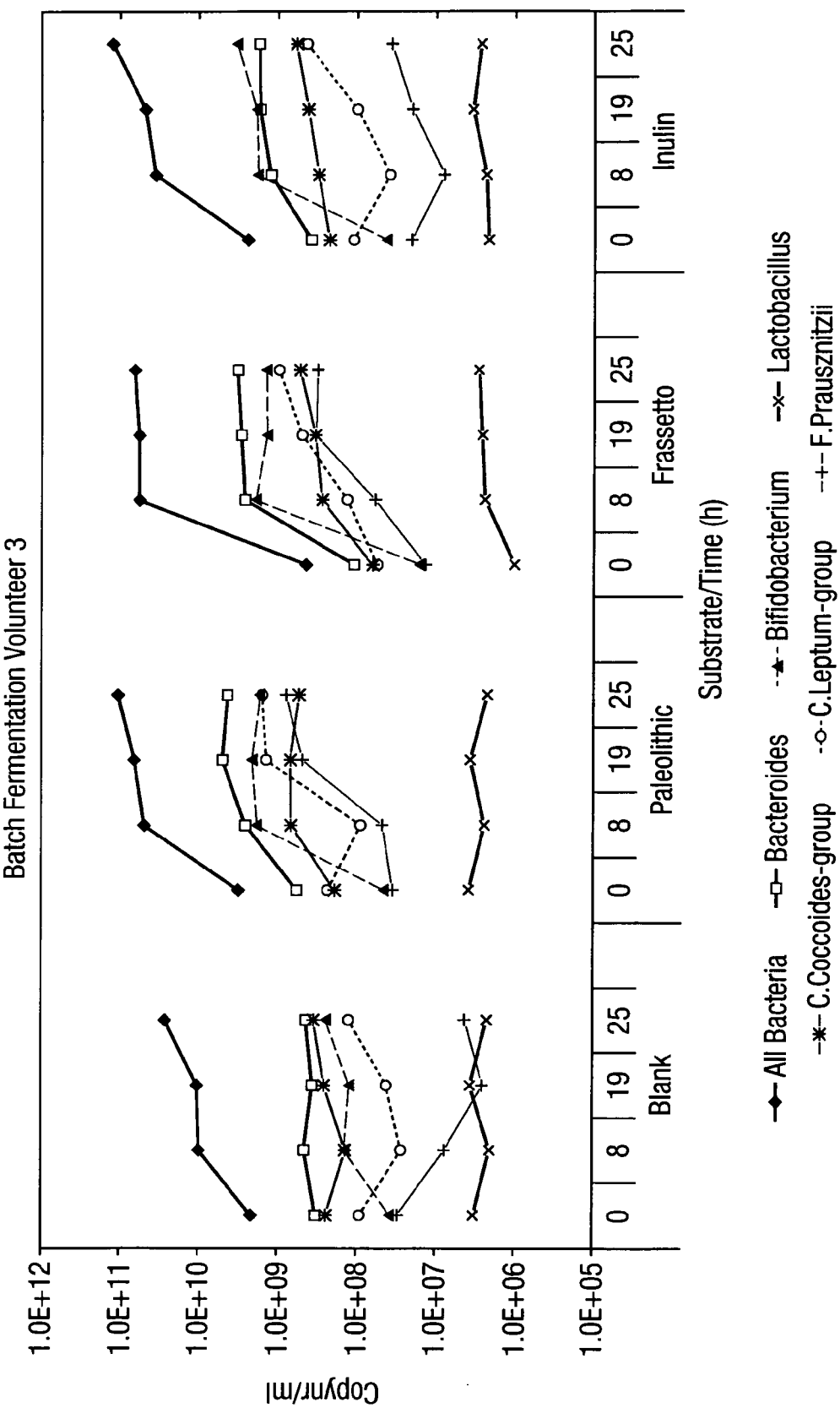

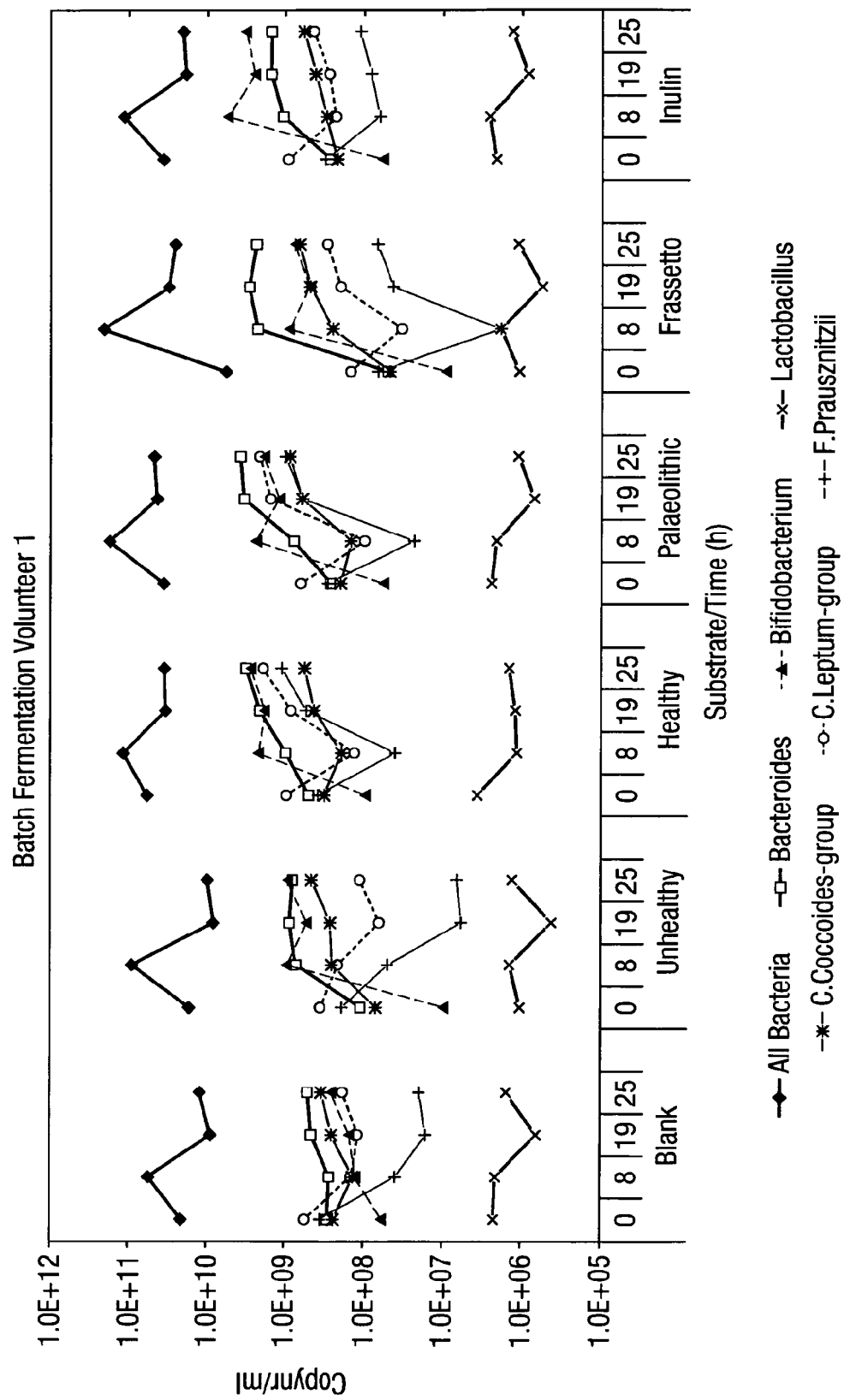

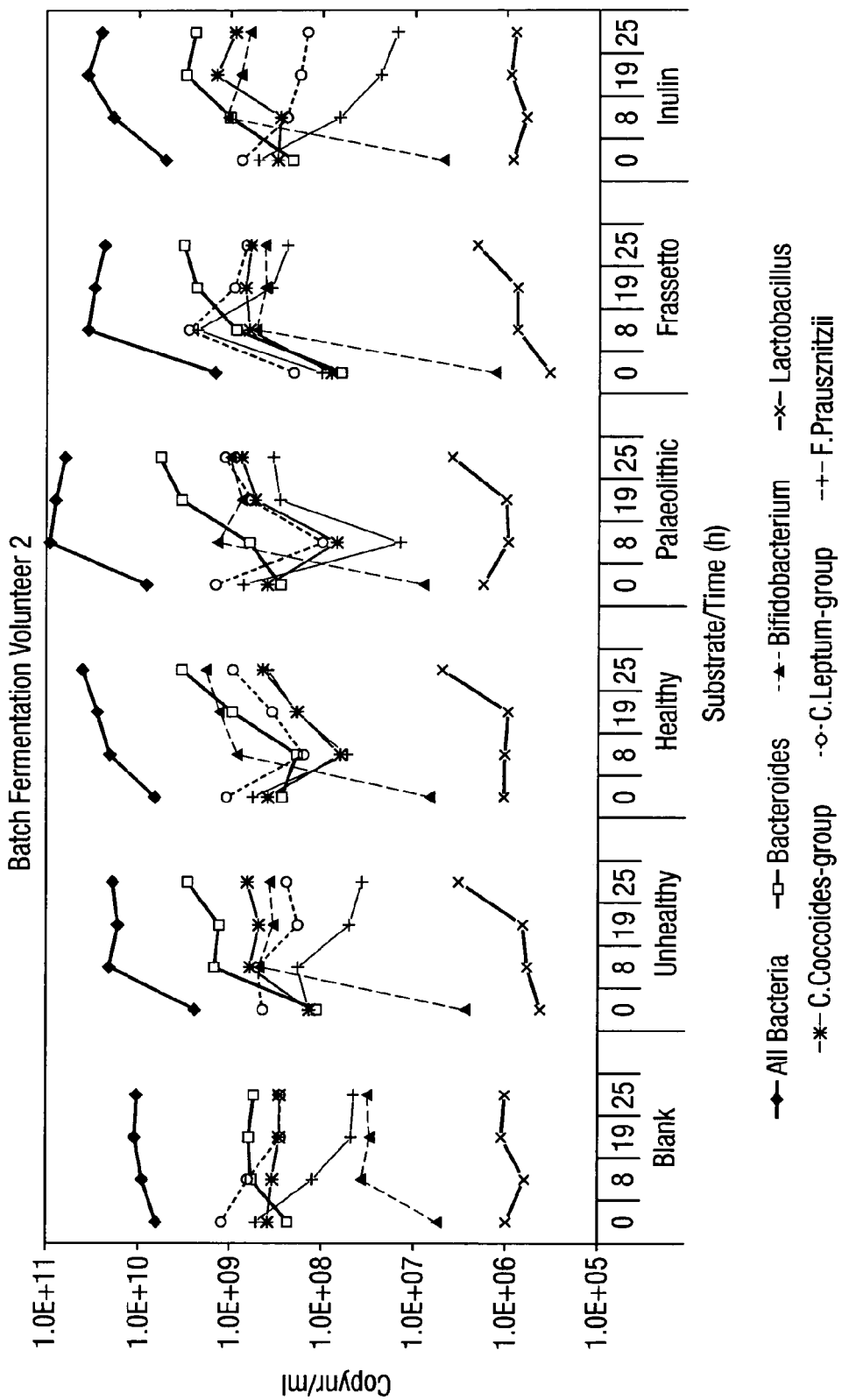

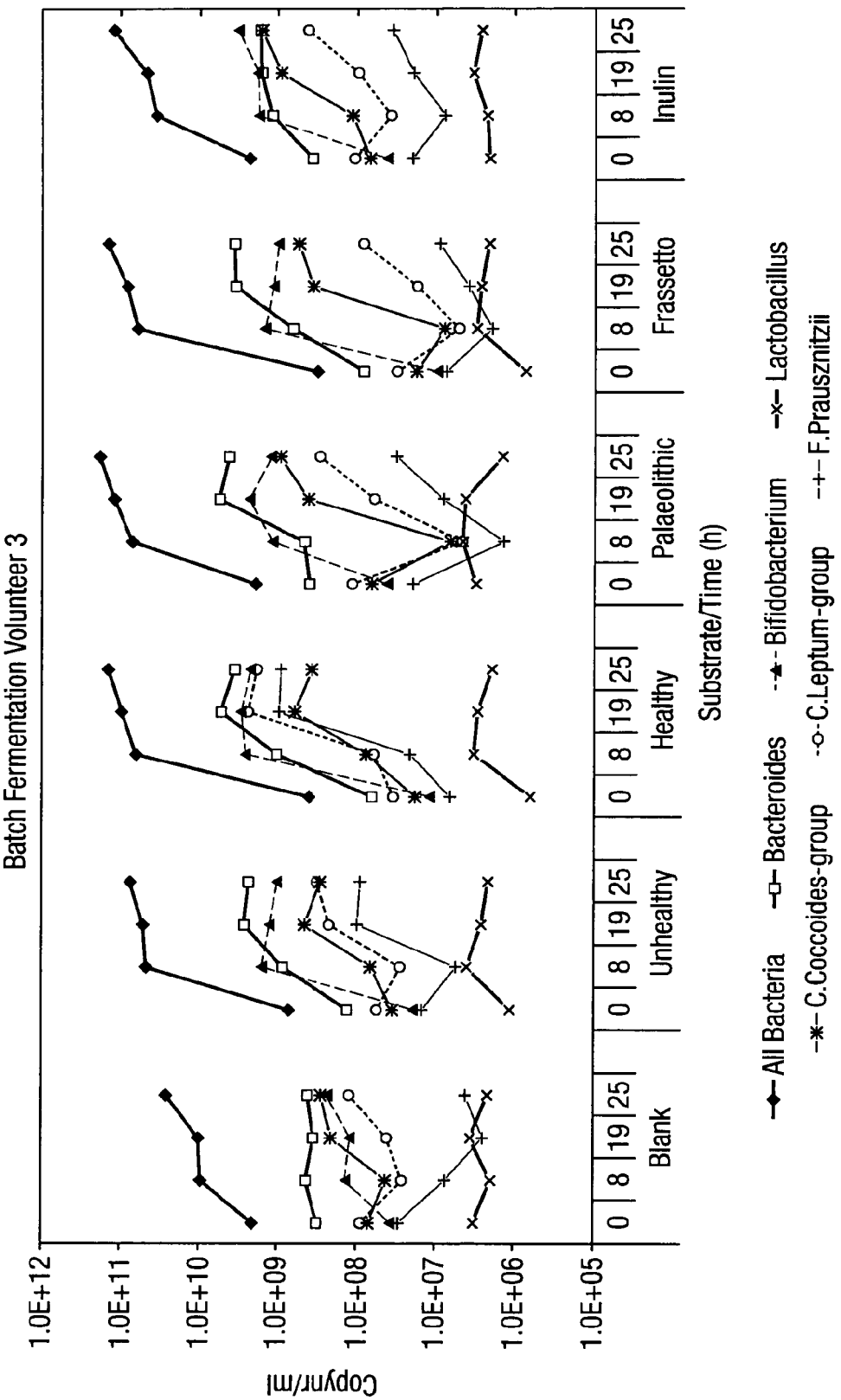

SEQUENCE LISTING

<160> NUMBER OF SEQ ID NOS: 20

<210> SEQ ID NO 1
<211> LENGTH: 19
<212> TYPE: DNA
<213> ORGANISM: Artificial sequence
<220> FEATURE:
<223> OTHER INFORMATION: Supplied by Applied Biosystems or Invitrogen

<400> SEQUENCE: 1
tcctacggga ggcagcagt                                              19

<210> SEQ ID NO 2
<211> LENGTH: 26
<212> TYPE: DNA
<213> ORGANISM: Artificial sequence
<220> FEATURE:
<223> OTHER INFORMATION: Supplied by Applied Biosystems or Invitrogen

<400> SEQUENCE: 2
ggactaccag ggtatctaat cctgtt                                      26

<210> SEQ ID NO 3
<211> LENGTH: 17
<212> TYPE: DNA
<213> ORGANISM: Artificial sequence
<220> FEATURE:
<223> OTHER INFORMATION: Supplied by Applied Biosystems or Invitrogen

<400> SEQUENCE: 3
ctcctggaaa cgggtgg                                                17

<210> SEQ ID NO 4
<211> LENGTH: 21
<212> TYPE: DNA
<213> ORGANISM: Artificial sequence
<220> FEATURE:
<223> OTHER INFORMATION: Supplied by Applied Biosystems or Invitrogen

<400> SEQUENCE: 4
ggtgttcttc ccatatctac a                                           21

<210> SEQ ID NO 5
<211> LENGTH: 21
<212> TYPE: DNA
<213> ORGANISM: Artificial sequence
<220> FEATURE:
<223> OTHER INFORMATION: Supplied by Applied Biosystems or Invitrogen

<400> SEQUENCE: 5
atagcctttc gaaagraaga t                                              21

<210> SEQ ID NO 6
<211> LENGTH: 21
<212> TYPE: DNA
<213> ORGANISM: Artificial sequence
<220> FEATURE:
<223> OTHER INFORMATION: Supplied by Applied Biosystems or Invitrogen

<400> SEQUENCE: 6
ccagtatcaa ctgcaatttt a                                              21

<210> SEQ ID NO 7
<211> LENGTH: 20
<212> TYPE: DNA
<213> ORGANISM: Artificial sequence
<220> FEATURE:
<223> OTHER INFORMATION: Supplied by Applied Biosystems or Invitrogen

<400> SEQUENCE: 7
aaatgacggt acctgactaa                                                20

<210> SEQ ID NO 8
<211> LENGTH: 22
<212> TYPE: DNA
<213> ORGANISM: Artificial sequence
<220> FEATURE:
<223> OTHER INFORMATION: Supplied by Applied Biosystems or Invitrogen

<400> SEQUENCE: 8
ctttgagttt cattcttgcg aa                                             22

<210> SEQ ID NO 9
<211> LENGTH: 16
<212> TYPE: DNA
<213> ORGANISM: Artificial sequence
<220> FEATURE:
<223> OTHER INFORMATION: Supplied by Applied Biosystems or Invitrogen

<400> SEQUENCE: 9
gcacaagcag tggagt                                                    16

<210> SEQ ID NO 10
<211> LENGTH: 18
<212> TYPE: DNA
<213> ORGANISM: Artificial sequence
<220> FEATURE:
<223> OTHER INFORMATION: Supplied by Applied Biosystems or Invitrogen

<400> SEQUENCE: 10
cttcctccgt tttgtcaa                                                  18

<210> SEQ ID NO 11
<211> LENGTH: 18
<212> TYPE: DNA
<213> ORGANISM: Artificial sequence
<220> FEATURE:
<223> OTHER INFORMATION: Supplied by Applied Biosystems or Invitrogen

```
<400> SEQUENCE: 11
agatggcctc gcgtccga                                                    18

<210> SEQ ID NO 12
<211> LENGTH: 19
<212> TYPE: DNA
<213> ORGANISM: Artificial sequence
<220> FEATURE:
<223> OTHER INFORMATION: Supplied by Applied Biosystems or Invitrogen

<400> SEQUENCE: 12
ccgaagacct tcttcctcc                                                   19

<210> SEQ ID NO 13
<211> LENGTH: 19
<212> TYPE: DNA
<213> ORGANISM: Artificial sequence
<220> FEATURE:
<223> OTHER INFORMATION: Supplied by Applied Biosystems or Invitrogen

<400> SEQUENCE: 13
agcagtaggg aatcttcca                                                   19

<210> SEQ ID NO 14
<211> LENGTH: 17
<212> TYPE: DNA
<213> ORGANISM: Artificial sequence
<220> FEATURE:
<223> OTHER INFORMATION: Supplied by Applied Biosystems or Invitrogen

<400> SEQUENCE: 14
caccgctaca catggag                                                     17

<210> SEQ ID NO 15
<211> LENGTH: 20
<212> TYPE: DNA
<213> ORGANISM: Artificial sequence
<220> FEATURE:
<223> OTHER INFORMATION: Supplied by Applied Biosystems or Invitrogen
<220> FEATURE:
<221> NAME/KEY: misc_feature
<222> LOCATION: (12)..(12)
<223> OTHER INFORMATION: m is a, or c

<400> SEQUENCE: 15
agagtttgat cmtggctcag                                                  20

<210> SEQ ID NO 16
<211> LENGTH: 20
<212> TYPE: DNA
<213> ORGANISM: Artificial sequence
<220> FEATURE:
<223> OTHER INFORMATION: Supplied by Applied Biosystems or Invitrogen
<220> FEATURE:
<221> NAME/KEY: misc_feature
<222> LOCATION: (15)..(15)
<223> OTHER INFORMATION: n is a, c, g, or t

<400> SEQUENCE: 16
aaggaggtga tccanccrca                                                  20

<210> SEQ ID NO 17
<211> LENGTH: 20
<212> TYPE: DNA
<213> ORGANISM: Artificial sequence
<220> FEATURE:
<223> OTHER INFORMATION: Supplied by Applied Biosystems or Invitrogen
```

```
<400> SEQUENCE: 17
tgattccgca tggtttcatt                                               20

<210> SEQ ID NO 18
<211> LENGTH: 20
<212> TYPE: DNA
<213> ORGANISM: Artificial sequence
<220> FEATURE:
<223> OTHER INFORMATION: Supplied by Applied Biosystems or Invitrogen

<400> SEQUENCE: 18
cgacccatag agccttcatc                                               20

<210> SEQ ID NO 19
<211> LENGTH: 18
<212> TYPE: DNA
<213> ORGANISM: Artificial sequence
<220> FEATURE:
<223> OTHER INFORMATION: Supplied by Applied Biosystems or Invitrogen

<400> SEQUENCE: 19
tcgagcggac catgatca                                                 18

<210> SEQ ID NO 20
<211> LENGTH: 19
<212> TYPE: DNA
<213> ORGANISM: Artificial sequence
<220> FEATURE:
<223> OTHER INFORMATION: Supplied by Applied Biosystems or Invitrogen

<400> SEQUENCE: 20
ggcggcgtct gagataaca                                                19
```

COMPOSITIONS FOR DIETARY HEALTH MANAGEMENT

This invention relates to a plurality of compositions for dietary health management and its use in the prevention or treatment of any one of the disease states in the group consisting of cardiovascular disease, inflammation and diarrhoea.

Human evolution has been a very slow process in contrast to the relatively recent, rapid changes in our diet since the Neolithic revolution which marked the switch from hunter-gatherer to agricultural life-style around 10,000 years ago. Moreover our genome has not had time to evolve at the same pace and therefore it is postulated that our bodies will work more efficiently with an ancestral diet.

Man first diverged from apes over 12 million years ago and from that period until the Neolithic period when agriculture first appeared, the various *Homo* species are assumed to have lived on wild fruit and vegetables (including leaves) and scavenged protein, then developing hunting as tools were developed (2 million years ago). *Homo erectus*, who emerged between 1.8 and 2 million years ago, is regarded as the first *Homo* species with many key humanlike traits. These include the large brain, that is thought to have been able to develop as a result of a switch to meat eating (initially scavenging and later hunting), but also a smaller gut and much smaller teeth and jaws. Wrangham (Catching fire: How cooking made us human. Profile (2009)) suggested that these changes not only indicate a switch to meat, but that they could also indicate that the use of fire to cook food was much earlier than has previously been thought, although the earliest evidence for controlled fire only goes back 250,000 years. If this theory is correct, it would not only explain some of our physical adaptations but also why humans do not appear to thrive on a completely raw food diet (see Koebnick C., Garcia, A. L., Dagnelie, P. C. and Strassner, C., J. Nutrit., 135, 2372-2378 (2005)) which would be expected if we had only been cooking our food for around 250,000 to 50,000 years, as previously thought. The use of cooking can also then be included quite happily in any Palaeolithic style diet. The Neolithic revolution then led to a switch to an agricultural way of life and a change in diet from high protein (animal protein) to high carbohydrate (cereal).

According to Laden, G. and Wrangham, R. (J. Hum. Evol., 49, 482-498 (2005)) evidence regarding the overall health of Palaeolithic man is more detailed than would initially be expected, as some evidence of overall health and lifestyle can be gleaned from bone samples, although the lack of soft tissue means that there is no surviving evidence for the prevalence of many diseases. In particular Cohen, M. N. (Health and the rise of civilization. Yale University Press (1989)) discloses bone records for Cro-Magnon man, the progenitor of the European population, which show that he was tall and suffered from fewer diseases than the Neolithic man he evolved into. Similar evidence for the decreased health of man as agriculture increased has also been found in the Americas where studies have shown an increase in the number of bone lesions associated with bacterial infections in skeletons of farming populations as opposed to hunter gatherers. This increase in level of infection is also associated with an increase in mortality, most markedly in the number of individuals surviving past the age of 45 decreasing from 13% down to 7% of the total population (see Larsen C S, "Skeletons in our closet: Revealing our past through Bioarchaeology" Princeton (2002) ISBN0-691-09284-2).

More importantly, some of the adaptations that have occurred and spread over the past couple of thousand years have served to worsen the situation in our current times of plenty. As a species developing agriculture and switching to a high starch cereal based diet, individuals best placed to survive harsh winters after a poor harvest as a result of laying down of high fat stores when carbohydrate was plentiful, would survive at the expense of their skinnier cousins. This "Thrifty gene hypothesis" proposed by Neel, J. V. (Am. J. Hum. Genet., 14, 353-362 (1962)), that specific genes have been selected that increase the efficiency of deposition of fat from available carbohydrate and suggests that individuals who can most efficiently lay down these fat stores will have been selected for resulting in a sub-population of people predisposed to obesity. Frayling, T. M. et al. (Science, 316, 889-894 (2007)) recently discovered several genotypes, including alleles of the FTO gene, which associate with obesity and Type 2 diabetes, would bear this theory out. The individuals inheriting these genotypes are now a population which is genetically predisposed to lay down fat stores continuously due to the freely available starch content of our diet. This in itself can be seen in the anecdotal evidence all around us of people who struggle to maintain their weight at a "healthy" level, while other individuals appear to be far less constrained in their diet without appearing to gain weight.

Despite the above, dietary guidelines issued by the World Health Organisation (WHO) and also the US Department of Agriculture (USDA) all recommend a diet which is high in carbohydrates (55-75% of consumed calories) and low in protein (10-15% of consumed calories), a direct contradiction of the proposed Palaeolithic diet, which is high in protein (30%) and low in carbohydrate.

Thus for the past 10,000 or so years, Man has been living a lifestyle to which he has not adapted and as a result is not at the physiological optimum that he could achieve if his diet was designed to complement the body his genes have created. Therefore we should return to a more Palaeolithic style diet in order to mitigate against the widespread incidence of modern afflictions, such as cardiovascular disease and type 2 diabetes, which currently threaten Man.

This concept of reverting to a Paleolithic type diet was initially put forward by Eaton et al. (New Eng. J. Med., 312, 283-289 (1985)) and initial clinical trials carried out by Frassetto et al (Eur. J. Clin. Nutrit., 63, 947-955 (2009)) showed improvements in arterial blood pressure and reduction of total cholesterol, low density lipoprotein (LDL) blood lipids and triglycerides. Improved glycaemic control and improvement in several cardiovascular risk factors were seen in the study by Jönssen et al (Cardiovasc. Diabetol., 8, 35-48 (2009)) although this study was conducted on diabetic patients, so there are reservations about extrapolating to normal individuals. The limitation with this latter study was that the participants were given overall dietary guidance. Specifically the diet should be based on should be based on lean meat, fish, fruit, leafy and cruciferous vegetables, root vegetables, eggs and nuts, while excluding dairy products, cereal grains, beans, refined fats, sugar, candy, soft drinks, beer and extra addition of salt. The following items were recommended in limited amounts: eggs (no more than 2 per day), nuts (preferentially walnuts), dried fruit, potatoes (no more than 1 medium-sized per day), rapeseed or olive oil (no more than 1 tablespoon per day), wine (no more than 1 glass per day).

In order to combat, at least in part, modern afflictions such as cardiovascular disease and type 2 diabetes, a diet based on the principles of the diet of Palaeolithic Man is proposed

SUMMARY OF THE INVENTION

In a first aspect of the invention, a plurality of compositions for the dietary health management system of a human being is provided, wherein the plurality of compositions comprise a daily diet of:
(a) 1750 to 2750 kilocalories (7350 to 11550 kiloJoules);
(b) have more than 1250, preferably more than 1450, more preferably more than 1650 mg gallic acid equivalents of polyphenols;
(c) have more than 40, preferably more than 50, more preferably more than 60 g fibre;
(d) have more than 130, preferably more than 150, more preferably more than 170 g protein
(e) have 0 to 2, preferably 0 to 1.5, most preferably 0 to 1 g starch; and
(f) have 0 to 5, preferably 0 to 2.5, most preferably 0 to 1 g lactose.

Each composition is a pre-prepared food or drink component (for example a pre-prepared savoury meal or dessert) which when added together form a daily diet, the compositions comprising a plurality of food or drink ingredients. The daily diet is characterised by normal levels of energy, but high levels of polyphenols, fibre and proteins and low levels of starch and lactose than the diet based on WHO guidelines (WHO technical report series no. 916 "Diet nutrition and the prevention of chronic diseases" (2003)".

Gallic acid equivalents of polyphenols is measured using Folin-Ciocalteu reagent.

The plurality of compositions may comprise a daily diet comprising less than 5000, preferably less than 4000, more preferably less than 3000 mg gallic acid equivalents of polyphenols. Furthermore they may also comprise a daily diet comprising less than 200, preferably less than 150, more preferably less than 100 g of fibre.

In addition, the plurality of compositions could comprise a daily diet comprising less than 250, preferably less than 225, more preferably less than 200 g of protein.

The plurality of compositions may comprise a daily diet of at least 110, preferably at least 130, most preferably at least 150 mg of at least one flavanoid. Whilst flavanoids are broadly associated with improved health, preferably the plurality of compositions comprise a daily diet of less than 500, preferably less than 400, more preferably less than 300 mg of at least one flavanoid.

The plurality of compositions may comprise a daily diet of at least 0.1, preferably at least 0.5, more preferably at least 1.0 mg of at least one anthocyanidin. Whilst anthocyanidin are also broadly associated with improved health, preferably the plurality of compositions comprise a daily diet of less than 300, preferably less than 200, more preferably less than 100 mg of at least one anthocyanidin.

In particular the plurality of compositions may comprise a daily diet additionally comprising a mixture of apigenin, cyanidin-3-glucoside, delphinidin, epicatechin, hesperetin, kaempferol, luteolin, pelargonidin-3-glucoside, quercetin, quercetin-3,4-diglucoside, quercetin-3-glucoside and quercetin-4-glucoside. A broad range of such flavanoids is generally considered to lead to better health because the flavanoids exhibit multiple anti-oxidant mechanisms which are likely to be more effective than a single anti-oxidant mechanism.

The plurality of compositions may comprise at least 110, preferably at least 120, most preferably at least 130 polyphenols.

Optionally the plurality of compositions can comprise a daily diet comprising an omega 6:omega 3 fatty acid ratio of less than 3:1, preferably less than 2:1. Whilst such a ratio is associated with better heart health, preferably the plurality of compositions comprise a daily diet of an omega 6:omega 3 fatty acid ratio of more than 1:10, preferably more than 1:5, more preferably 1:2.

The plurality of compositions may also comprise a daily diet additionally comprising a potassium:sodium ratio of more than 4:1, preferably more than 5:1, most preferably more than 6:1 with the proviso that the weight of sodium is 0.5 to 2.5 g. Such a ratio is associated with heart health and an optimal blood pressure osmotic balance. However it is preferable if the plurality of compositions comprise a daily diet comprising an potassium:sodium ratio of less than 11:1, preferably less than 10:1, most preferably less than 9:1

In a second aspect of the invention, a plurality of compositions according to the first aspect of the invention is provided for use as a medicament.

In a third aspect of the invention, a plurality of compositions according to the first aspect of the invention is provided for use in the prevention or treatment of any one of the disease states in the group consisting of cardiovascular disease, type 2 diabetes, inflammation, diarrhoea and bone health. By the term "bone health" is meant improved bone mass and bone density.

In a fourth aspect of the invention is provided use of a plurality of compositions in accordance with the first aspect of the invention for the manufacture of a medicament for the prevention or treatment of any one of the disease states in the group consisting of cardiovascular disease, type 2 diabetes, inflammation, diarrhoea and bone health.

In a fifth aspect of the invention is provided a method for the prevention or treatment of any one of the disease states in the group consisting of cardiovascular disease, type 2 diabetes, inflammation, diarrhoea and bone health, the method comprising the step of administering to a person in need therefor the plurality of compositions of the first aspect of the invention.

BRIEF DESCRIPTION OF THE INVENTION

The invention is illustrated with reference to the following figure in which:

FIG. 1 shows the qPCR results for copy number per mL for *Bacteroides, Bifidobacterium, Lactobacillus, C. coccoides*-group, *C. leptum*-group, *F. prausznitzii* and all bacteria following batch fermentation of various diets ("blank" means no food diet, "unhealthy" means unhealthy diet, "healthy" means diet based on WHO guidelines, "Paleolithic" means Paleolithic based diet and "inulin" means diet based on inulin) using faecal matter from two volunteers; and FIG. 2 shows changes in the log intensity values over time ("t" in hours) for *Aeromonas* sp. and *Bacteroides fragilis* generated by HITchip analysis for the unhealthy diet ("unhealthy" left-hand bar)), the diet based on WHO guidelines ("healthy" middle bar) and the Paleolithic based diet ("Paleolithic" right-hand bar).

FIG. 3 *a-c* shows changes in the log intensity values over time for the indicated bacterial species generated by HITchip analysis for the unhealthy diet ("unhealthy"), the diet based on WHO guidelines ("healthy") the Paleolithic based diet ("Paleolithic"), the diet disclosed in the Frassetto paper ("Fressetto"), and the diet based on inulin ("Inulin"), for three volunteers, wherein the data for volunteers 1-3 are presented in panels a-c respectively.

Figure 4A:
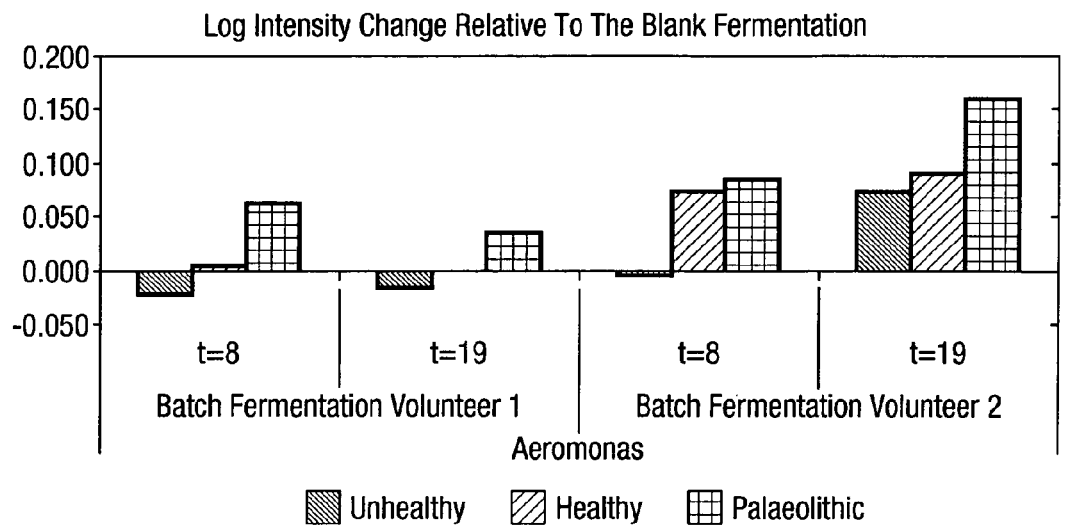
Figure 4B:
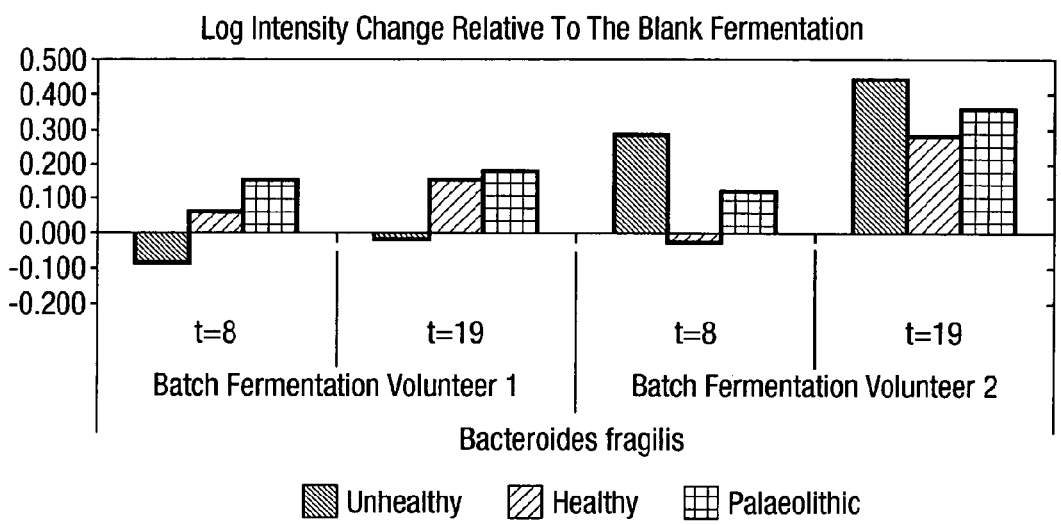

FIG. 4 *a-b* shows the log intensity change at the time (t) indicated for 2 volunteers for Aeromonas sp (FIG. 4*a*) and Bacteroides fragilis (FIG. 4b) for the following diets: unhealthy diet ("unhealthy" left-hand bar)), the diet based on WHO guidelines ("healthy" middle bar) and the Paleolithic based diet ("Paleolithic" right-hand bar), relative to the log intensity change at the time (t) indicated blank (no food diet).

DETAILED DESCRIPTION OF THE INVENTION

Diets

The following diets were designed with all diets normalised to approximately 2400 kcal per day:

TABLE 1a

| Unhealthy diet | |
|---|---|
| Unhealthy | |
| Breakfast | toast and butter |
| | glass of milk |
| Lunch | cheese sandwich |
| | bar of chocolate |
| Dinner | sausages, chips and beans |
| Snack | rice pudding |

TABLE 2a

| Diet based on WHO guidelines (WHO technical report series no 916 "Diet, nutrition and the prevention of chronic diseases" (2003)) | |
|---|---|
| WHO | |
| Breakfast | Cheerios cereal and milk |
| | toast and Flora Pro-Active light margarine |
| Lunch | rice and bean salad |
| | banana |
| Dinner | orange juice |
| | haddock and oven chips with carrots |
| Snack | Twix chocolate bar |

TABLE 3a

| Paleolithic based diet | |
|---|---|
| Palaeolithic | |
| Breakfast | salmon omelette |
| | half a grapefruit |
| Lunch | mixed green vegetable soup with prawns |
| | strawberries and cherries |
| Dinner | chicken and ratatouille |
| | baked apple with blueberries and honey |
| Snacks | celery and carrot sticks |
| | hazelnuts, dried apricots and figs |

TABLE 4a

| Diet based on Frassetto paper (see earlier) | |
|---|---|
| Frassetto | |
| Breakfast | pork and pineapple with honey |
| | carrot juice |
| Lunch | tuna salad |
| | tomato soup |
| Dinner | chicken stir fry with broccoli and garlic |
| | tomato soup |
| | roast parsnips and mushrooms |
| Snacks | carrot juice |
| | cantaloupe melon |
| | almonds |
| | turkey guacamole and tomato lettuce rollups |

These diets translated into the following amounts of ingredients:

TABLE 1b

| Ingredients of unhealthy diet | |
|---|---|
| Ingredient | Weight (g) |
| Baked beans | 84 |
| Butter, salted | 10 |
| Cheddar cheese | 132 |
| Milk | 240 |
| Milk chocolate | 44 |
| Oven chips | 100 |
| Pork sausage | 200 |
| Ready to eat rice pudding | 113 |
| Sugar | 30 |
| White bread | 108 |

TABLE 2b

| Ingredients of WHO recommended diet | |
|---|---|
| Ingredient | Weight (g) |
| Banana | 136 |
| Carrots | 100 |
| Cheerios (cereal) | 50 |
| Flora Pro-Active light margarine | 5 |
| Grilled haddock | 120 |
| Milk | 300 |
| Multigrain bread | 41 |
| Olive oil | 14 |
| Orange juice | 200 |
| Oven chips | 18 |
| Red kidney beans | 150 |
| Sweet red peppers | 40 |
| Tomatoes | 40 |
| Twix bar (2 sticks) | 58 |
| White long grain rice | 300 |

TABLE 3b

| Ingredients of Paleolithic based diet | |
|---|---|
| Food | Weight (g) |
| Aubergine | 150 |
| Broccoli | 50 |
| Brown flaxseeds | 10 |
| Carrots | 80 |
| Celery | 80 |
| Celery seeds | 3 |
| Chicken breast, meat only, no skin | 250 |
| Dried blueberries with apple juice | 30 |
| Dried figs | 50 |
| Dried unsulphured apricots | 50 |
| Egg | 100 |
| Farmed Atlantic salmon | 200 |
| Fresh basil | 10 |
| Garlic | 1.5 |
| Ginger root | 12.5 |
| Grapefruit (pink Florida) | 123 |
| Hazelnuts | 20 |
| Honey | 10 |
| Kiwi fruit | 76 |
| Onions | 137 |
| Peas (frozen) | 38 |
| Raw apple with skin | 222 |
| Savoy cabbage | 50 |
| Seedless raisins | 30 |
| Shrimps/prawns | 150 |
| Spinach | 31 |
| Strawberries | 100 |
| Sweet cherries | 100 |
| Sweet yellow peppers | 60 |
| Tahini (sesame seed butter) | 28 |
| Tomatoes | 338 |
| Watercress | 19 |
| White mushrooms | 72.5 |

TABLE 4b

Ingredients of diet based on Frassetto paper (see earlier)

| Food | Weight (g) |
|---|---|
| Avocado | 34 |
| Broccoli | 186 |
| Campbell's tomato soup | 300 |
| Carrot juice (jar) | 600 |
| Chicken breast (meat only) | 250 |
| Tuna | 250 |
| Garlic | 3 |
| Honey | 21 |
| Lettuce (iceberg) | 120 |
| Melon (Cantaloupe) | 120 |
| Mushrooms | 100 |
| Nuts (almonds) | 70 |
| Olive Oil | 30 |
| Parsnips | 120 |
| Pineapple | 200 |
| Pork tenderloin lean only | 140 |
| Radishes | 4 |
| Hellman's light mayonnaise | 20 |
| Shallots | 12 |
| Thyme (dried) | 1 |
| Spinach | 36 |
| Tomatoes (red ripe) | 160 |
| Turkey (light meat no skin) | 50 |

Chemical Analysis of Diets

The menu food for each full day was frozen in liquid nitrogen, freeze-dried and ground in a homogenizer. Assays for ascorbic acid, total phenolics (bound and unbound), individual flavanoids, sugars and starch.

(a) Ascorbic Acid Assay

This assay was based on the methods of Foyer et al. (Plant Physiol., 109, 1047-1057 (1995)) and Hewitt, E. J. et al (Biochem. J., 78, 384-391 (1961)). Briefly, the freeze-dried, ground material was added to 3.5-fold (v/w) of MPA/EDTA (5% (w/v) metaphosphoric acid+1 mM tetrasodium ethylenediaminetetracetic acid) and left on ice for 30 minutes. The suspension was centrifuged for 1 minute at 11,000×g in a microfuge to remove debris and precipitate. 0.25 mL of the supernatant was added to 2.25 mL sodium phosphate buffer (1 M pH 6.0) and the $A_{265}$ (absorbance at 265 nm) measured. 25 μL of ascorbate oxidase (400 $U \cdot mL^{-1}$ in phosphate buffer) was added and mixed. The $A_{265}$ was measured again and the decrease in absorbance calculated. The method was calibrated using 0 to 1 mM ascorbate standards in MPA/EDTA.

(b) Total Polyphenols Assay

This assay was based on the Folin-Ciocalteu method as modified by Velioglu, Y. S. et al. (J. Agric. Food Chem., 46, 4113-4117 (1998)) and Vinson, J. A. et al. (J. Agric. Food Chem., 46, 3630-3634 (1998)). Briefly, 500 mg of the freeze-dried, ground material was added to 5 mL of 70% (v/v) aqueous methanol and shaken in a sealed centrifuge tube for 2 hours at 22 degrees centigrade. The suspension was centrifuged at 1,000×g for 10 minutes at 15 degrees centigrade and the supernatant filtered through a 0.45 μm filter. The filtrate was stored at −20 degrees centigrade until assay. 5 mL of methanolic hydrochloric acid (50% methanol+50% 1.2 M HCl) was added to the precipitate which was then resuspended and heated in the sealed centrifuge tube for 2 hours at 90 degrees centigrade. After cooling, the suspension was centrifuged at 1,000×g for 10 minutes at 15 degrees centigrade and the supernatant filtered through a 0.45 μm filter.

200 μL aliquots of the filtrates were added to 1.5 mL of Folin-Ciocalteu reagent (0.2 M aqueous solution) and allowed to stand at 22 degrees centigrade for exactly 5 minutes. 1.5 mL of sodium bicarbonate solution (6% (w/v) and allowed to stand at 22 degrees centigrade for 90 minutes. The solutions were centrifuged at 1,000×g for 10 minutes at 15 degrees centigrade to remove haze and the absorbances measured at 765 nm. The $A_{765}$ were compared with gallic acid standards (0 to 0.2 $mg \cdot ml^{-1}$) in aqueous methanol or methanolic hydrochloric acid as appropriate. Total polyphenol concentrations are expressed as Gallic Acid Equivalents.

This assay also provided figures for conjugated (ie bound) and free polyphenols.

(c) Individual Flavanoids Assay

This work was carried out by under contract at Cranfield University. Briefly, lipids were removed from the freeze-dried, ground material by the method of Meyer, M. D. et al., (J. Agric. Food Chem., 56, 7439-7445 (2008)) and flavanoids extracted and assayed by HPLC as detailed in Downes, K. et al., (Postharvest Biol. Technol., 54, 80-86 (2009)) for flavonoids and as detailed in Giné Bordonaba, J et al., (J. Agric. Food Chem., 56, 7422-7430 (2008)) for anthocyandins. Components were detected by diode array with reference to known standards.

(d) Sugars Assay

This assay was based on the Lactose/Sucrose/D-Glucose Assay Procedure (K-LACSU) supplied by Megazyme International. Briefly, 500 mg of the freeze-dried, ground material were added to 5 mL of aqueous ethanol and incubated at 85-90 degrees centigrade for 5 minutes. The suspension was quantitatively transferred to a 50 mL volumetric flask and the volume adjusted to 50 mL with sodium acetate buffer (50 mM sodium acetate (pH 4.5)+5 mM calcium chloride) and mixed thoroughly. An aliquot was centrifuged for 1 minute at 11,000×g in a microfuge and 1 mL of the supernatant added to 3 mL of distilled water. This solution was mixed thoroughly and 0.2 mL added to the bottom of three test tubes. One of the following was added to each of the tubes: 0.2 mL of sodium acetate buffer (D-glucose determination), 0.2 mL of β-fructosidase (10 $U \cdot mL^{-1}$ β-fructosidase in 5% glycerol, 0.1 $mg \cdot mL^{-1}$ bovine serum albumin and 0.02% sodium benzoate in sodium acetate buffer), (sucrose+D-glucose determination) or 0.2 mL β-galactosidase (380 $U \cdot mL^{-1}$ β-galactosidase in sodium acetate buffer), (lactose+D-glucose determination). Tubes (including reagent blanks and D-glucose controls) were incubated at 50 degrees centigrade for 20 minutes and 3.0 mL of GOPOD solution (>0.3 $U \cdot mL^{-1}$ glucose oxidase, >0.016 $U \cdot mL^{-1}$ peroxidase and 2 $\mu g \cdot mL^{-1}$ aminoantipyrine in 25 mM potassium phosphate buffer (pH 7.4)+5.5 mM p-hydroxybenzoic acid and 0.01% sodium azide) added to all tubes and incubated at 50 degrees centigrade for a further 20 minutes. The absorbances were measured at 510 nm and the sugar contents calculated.

(e) Starch Assay

This assay was based on the Total Starch Assay Procedure (K-TSTA) supplied by Megazyme International. Briefly, 100 mg of the freeze-dried, ground material was added to 5 mL of 80% (v/v) aqueous ethanol and incubated at 80-85 degrees centigrade for 5 minutes. The suspension was mixed and a further 5 mL of aqueous ethanol added. The tubes were centrifuged for 10 minutes at 1,800×g and the supernatant discarded. The pellet was re-suspended in aqueous ethanol and stirred. The suspension was centrifuge as before and the supernatant discarded. The pellet was re-suspended in 2 mL of 2 M potassium hydroxide and stirred for approximately 20 minutes in an ice/water bath. 8 mL of sodium acetate buffer (1.2 M sodium acetate (pH 3.8)) was added with stirring and 0.1 mL of α-amylase solution (3,000 $U \cdot mL^{-1}$ thermostable α-amylase on Ceralpha reagent (blocked p-nitrophenyl maltoheptaoside)) and 0.1 mL of aminoglucosidase solution (3,300 U·mL$^{-1}$ amyloglucosidase on p-nitrophenyl β-maltoside) added immediately. The suspension was mixed well and incubated at 50 degrees centigrade for 30 minutes with intermittent vortexing. The suspension was quantitatively transferred to a 100 mL volumetric flask and the volume adjusted to 100 mL. The flask was mixed well and an aliquot of the solution were centrifuged for 1 minute at 11,000×g in a microfuge. 0.1 mL of the aliquot were transferred to a test tube and 3.0 mL of GOPOD solution added. The tube (together with glucose standard solutions and reagent blanks) was incubated for 20 minutes at 50 degrees centigrade. The absorbance was measured at 510 nm and the starch content calculated.

(f) Carotenoid Assay

The assay was carried out by Intertek ASG (Manchester, England). Briefly, 0.5 g of the freeze-dried, ground material was extracted in 20 mL acetone with ultrasonication for 30 minutes. Individual carotenoids were separated on an Agilent 1200 Series HPLC with Diode Array Detection and peaks compared with commercially available known standards.

(g) Fibre Assay

This assay was carried out using the Megazyme Total Dietary Fibre Assay Procedure (K-TDFR, AOAC Method 991.43) supplied by Megazyme International. Briefly, duplicate 1 g freeze-dried, ground material (defatted with 3 extractions in iso-hexane and dried) were accurately weighed into beakers and dispersed in 40 mL of buffer (50 mM 2-(N-morpholino)ethanesulfonic acid (MES)+50 mM tris(hydroxymethyl)aminomethane (tris), pH 8.2 at 24 degrees centigrade). 0.05 mL of heat-stable α-amylase solution (~10,000 U·ml$^{-1}$) was added, while stirring at low speed. Each beaker was covered with aluminium foil squares and placed in a shaking water bath at 95 degrees centigrade for 35 minutes with continuous agitation. The beakers were removed and cooled to 60 degrees centigrade. The side walls of the beakers and spatula were rinsed in 10 mL of water and 0.1 mL of protease solution (~350 U·ml$^{-1}$) was added to each beaker and incubated at 60 degrees centigrade for 30 minutes with agitation. 5 mL of 561 mM hydrochloric acid was added to each beaker with stirring and the pH adjusted to between 4.1-4.8. 0.2 mL of amyloglucosidase solution (3,300 U·ml$^{-1}$) was added and the beakers incubated at 60 degrees centigrade for 30 minutes with agitation. The enzyme mixtures were filtered through pre-weighed crucibles containing 1 g of silica (Celite) and the residue washed twice with 10 mL of distilled water preheated to 70 degrees centigrade. The filtrate and water washings were retained for determination of soluble fibre. The insoluble fibre residues were washed twice with 10 mL of ethanol, then 10 mL of acetone, then dried overnight in a 103 degrees centigrade oven and weighed (insoluble fibre). 4 volumes of 96% ethanol at 60 degrees centigrade were added to the filtrate containing the soluble fibre and a precipitate allowed to form at room temperature for 60 minutes. The mixtures were filtered through pre-weighed crucibles containing 1 g of Celite and the residue washed twice with 15 mL of 78% ethanol, twice with 15 mL of 96% ethanol and twice with 15 mL of acetone. The crucibles were then dried overnight in a 103 degrees centigrade oven and weighed (soluble fibre). One set of crucibles were incinerated at 525 degrees centigrade for 5 hours to determine the ash content and the remaining set were assayed for protein using the Lowry assay for insoluble proteins (Lowry, O. H. et al., J. Biol. Chem. 193, 265-275 ((1951)). Ash and protein contents were subtracted from the apparent fibre weights to give true fibre values. Blank assays were run in parallel to eliminate reagent effects. Total fibre was the sum of the soluble and insoluble weights.

Results of Chemical Analysis

Table 5 summarises the results of the chemical analysis.

The unhealthy diet (UH) contained moderate amounts of polyphenolic/antioxidant compounds (615 mg GAE·diet$^{-1}$), with a vitamin C level surprisingly above the UK Recommend Daily Allowance of 60 mg. However the individual flavanoids assayed were not detectable suggesting that the total phenolic assay was only detecting non-flavanoid antioxidants in this sample. Starch, sucrose and lactose levels were relatively high in this diet, reflecting its 'processed food'/dairy-containing composition. Glucose levels were relatively low, reflecting the lack of vegetable material, particularly fruit.

The diet based on WHO guidelines (HE) contained higher levels of both polyphenolic/antioxidant compounds (998 mg GAE·diet$^{-1}$) and vitamin C (176 mg·diet$^{-1}$). It also contained 6 of the 14 assayed flavanoids. Again, starch, sucrose and lactose levels were relatively high in this diet due to the inclusion of a large quantity of carbohydrates specified in the WHO guidelines and the dairy component. Contrary to the unhealthy diet, glucose levels were moderately high, reflecting the inclusion of vegetable material.

For the diet based on the Frassetto paper (FR), the levels of both polyphenolic/antioxidant compounds and vitamin C were comparable to the HE diet (990 mg GAE·diet$^{-1}$ and 153 mg·diet$^{-1}$, respectively). It also contained 6 of the 14 assayed flavanoids, but not the same six as the HE diet, i.e. epicatechin and quercetin-3,4-diglucoside in place of kaempferol and quercetin. Carotenoids were also assayed with β-carotene, lycopene and xanthophyll being detected at significant levels. As would be expected from such a diet, levels of starch and lactose were low, reflecting the lack of processed carbohydrates and dairy products. Glucose levels were high, due to the inclusion of high amounts of vegetable material. Somewhat surprisingly, sucrose levels were fairly high, possibly due to the processed tomato soup. The significant levels of lactose probably also arose from the inclusion of the soup.

The Palaeolithic based diet (PA) contained levels of both polyphenolic/antioxidant compounds and vitamin C higher than the HE or FR diets (1719 mg GAE·diet$^{-1}$ and 353 mg·diet$^{-1}$, respectively) and contained 9 of the 14 assayed flavanoids, with the profile differing from both the HE and FR diets. This reflects the higher levels of plant material in the Palaeolithic based diet compared with the others. Carotenoids were also assayed with β-carotene, lycopene and xanthophyll being detected at significant levels, but with lower lycopene levels than the FR diet due to the latter's reliance on tomato soup. Levels of sugar and starch in the Palaeolithic based diet followed the trends of the diet based on the Frassetto paper, but the levels of starch, sucrose and lactose were lower (with lactose not significantly different from zero), reflecting a more strict adherence to a Palaeolithic diet. The higher level of glucose is almost certainly due to the larger proportion of fruit in this diet. The levels of total fibre was similar to that of the diet based on Frassetto paper and superior to those of the unhealthy diet or the diet based on WHO guidelines. A high fibre diet is generally considered to lead to higher retention times of nutrients in the gut which, in turn, leads to a higher level of absorbance of nutrients through the gut wall. Furthermore soluble fibre is broken down into short chain fatty acids which in turn provide a good environment for bacteria.

TABLE 5

Results of chemical analysis of daily diets ("UH" means unhealthy diet, "HE" means diet based on WHO guidelines, "FR" means diet based on Frassetto paper and "PA" means Paleolithic based diet; "GAE" means Gallic Acid Equivalents; "na" means not assayed; "nd" means not detected; *Values are means of two determinations ± standard deviations (SD) otherwise values are means of three determinations ± SD)

| | UH | HE | FR | PA |
|---|---|---|---|---|
| Antioxidants | | | | |
| Conjugated polyphenols (mg GAE · $diet^{-1}$) | 330 ± 13 | 728 ± 15 | 492 ± 18 | 764 ± 58 |
| Free polyphenols (mg GAE · $diet^{-1}$) | 285 ± 0 | 270 ± 5 | 498 ± 6 | 955 ± 23 |
| Total polyphenols (mg GAE · $diet^{-1}$) | 615 ± 13 | 998 ± 28 | 990 ± 38 | 1719 ± 137 |
| Vitamin C (mg · $diet^{-1}$) | 74 ± 3 | 176 ± 5 | 153 ± 12 | 353 ± 22 |
| Carbohydrates | | | | |
| Starch (g · $diet^{-1}$) | 8.22 ± 0.26 | 20.19 ± 0.17 | 2.50 ± 0.22 | 0.45 ± 0.03 |
| Glucose (g · $diet^{-1}$) | 1.19 ± 0.10 | 11.9 ± 0.5 | 39.5 ± 0.2 | 59.5 ± 1.2 |
| Sucrose (g · $diet^{-1}$) | 60.6 ± 1.7 | 54.9 ± 1.2 | 63.5 ± 0.7 | 19.3 ± 2.7 |
| Lactose (g · $diet^{-1}$) | 29.4 ± 0.4 | 26.7 ± 1.0 | 11.2 ± 0.3 | 0.30 ± 0.52 |
| Carotenoids | | | | |
| Lycopene (mg · $diet^{-1}$) | 0.9 ± 0.0* | 1.3 ± 0.2* | 19.8 ± 0.0* | 5.8 ± 0.0* |
| Xanthophyll (mg · $diet^{-1}$) | 0.0 ± 0.0* | 0.5 ± 0.0* | 4.5 ± 0.3* | 6.7 ± 0.3** |
| β-Carotene (mg · $diet^{-1}$) | 0.2 ± 0.2* | 11.2 ± 0.0* | 16.5 ± 0.3* | 13.3 ± 0.0* |
| Flavanoids | | | | |
| Apigenin (mg · $diet^{-1}$) | nd | 3.60 ± 0.43 | 9.49 ± 2.32 | nd |
| Cyanidin-3-glucoside (mg · $diet^{-1}$) | nd | nd | nd | 60.6 ± 4.19 |
| Cyanidin-3-rutinoside (mg · $diet^{-1}$) | nd | nd | nd | 2.67 ± 0.448 |
| Delphinidin (mg · $diet^{-1}$) | nd | nd | nd | nd |
| Epicatechin (mg · $diet^{-1}$) | nd | nd | 58.8 ± 17.8 | 64.6 ± 13.7 |
| Hesperetin (mg · $diet^{-1}$) | nd | nd | nd | nd |
| Kaempferol (mg · $diet^{-1}$) | nd | 0.29 ± 0.01 | nd | nd |
| Luteolin (mg · $diet^{-1}$) | nd | nd | nd | nd |
| Myricetin (mg · $diet^{-1}$) | nd | 0.43 ± 0.03 | 2.20 ± 0.11 | 3.25 ± 0.20 |
| Pelargonidin-3-glucoside (mg · $diet^{-1}$) | nd | nd | nd | 21.4 ± 1.14 |
| Quercetin (mg · $diet^{-1}$) | nd | 0.35 ± 0.01 | nd | 2.86 ± 0.10 |
| Quercetin-3,4-diglucoside (mg · $diet^{-1}$) | nd | nd | 7.71 ± 0.58 | 65.0 ± 1.23 |
| Quercetin-3-glucoside (mg · $diet^{-1}$) | nd | 3.21 ± 0.11 | 4.26 ± 0.17 | 18.8 ± 0.73 |
| Quercetin-4-glucoside (mg · $diet^{-1}$) | nd | 2.21 ± 0.15 | 8.04 ± 0.81 | 29.6 ± 0.92 |
| Fibre | | | | |
| Insoluble fibre (g · $diet^{-1}$) | 11.5 ± 0.3* | 35.0 ± 0.7* | 57.2 ± 9.3* | 54.8 ± 5.70* |
| Oligofructans (g · $diet^{-1}$) | 1.74 ± 0.39 | 2.90 ± 0.31 | 5.05 ± 0.04 | 6.68 ± 0.18 |
| Soluble fibre (g · $diet^{-1}$) | 3.2 ± 0.2* | 6.4 ± 0.2* | 5.4 ± 0.3* | 6.9 ± 2.2* |
| Total fibre (g · $diet^{-1}$) | 14.7 ± 0.4* | 41.4 ± 0.7* | 62.6 ± 9.3* | 61.7 ± 6.1* |

Table 6 summarise further compositional data relating to the diets obtained from Nutrientdata.com.

TABLE 6

Compositional data relating to the diets obtained from Nutrientdata.com ("UH" means unhealthy diet, "HE" means diet based on WHO guidelines, "FR" means diet based on Frassetto paper and "PA" means Paleolithic based diet)

| Nutrient | UH | HE | FR | PA |
|---|---|---|---|---|
| Kilocalories | 2,433 | 2,435 | | 2,414 |
| Protein (% of energy) | 18 | 14 | 30 | 30 |
| Carbohydrate (% of energy) | 30 | 62 | | 41 |
| Sugar (g) | 92 | 86 | | 169 |
| Sucrose (g) | 4.5 | 10 | | 17 |
| Glucose (g) | 1.4 | 9.6 | | 67 |
| Fructose (g) | 1.3 | 9.6 | | 62 |
| Lactose (g) | 13 | 0.2 | | 0.2 |
| Total fat (% of energy) | 52 | 24 | | 29 |
| Saturated fat (% of energy) | 25 | 9 | | 5.4 |
| Polyunsaturated fat (% of energy) | 5 | 2.4 | | 8.8 |
| Trans fat (% of energy) | 0 | 0 | | 0 |
| Monounsaturated fat (% of energy) | 18 | 10 | | 10.8 |

TABLE 6-continued

Compositional data relating to the diets obtained from Nutrientdata.com ("UH" means unhealthy diet, "HE" means diet based on WHO guidelines, "FR" means diet based on Frassetto paper and "PA" means Paleolithic based diet)

| Nutrient | UH | HE | FR | PA |
|---|---|---|---|---|
| ω-6 fatty acids (g) | 11 | 5.1 | 17 | 8.7 |
| ω-3 fatty acids (g) | 1.3 | 1.1 | 1.6 | 14 |
| ω-6/ω-3 ratio | 8.7 | 4.6 | 10.6 | 0.6 |
| Potassium (g) | 2.1 | 4.5 | | 7.2 |
| Sodium (g) | 4.0 | 1.5 | | 0.92 |
| Potassium/Sodium ratio | 0.53 | 3.05 | | 7.8 |

From table 6 it is apparent that the protein:carbohydrate:fat ratio of the Paleolithic based diet was 30:41:29 with the polyunsaturated to saturated fat ratio being 1.6 (close to the 1.4 proposed by Eaton et al.). The protein levels translate into 109 g/daily diet for the unhealthy diet, 79 g/daily diet for the diet based on WHO guidelines and 182 g/daily diet for the Paleolithic based diet. The sodium level is comparatively low. One feature of the Palaeolithic diet is the low of ω-6:ω-3 fatty acids ratio which is at odds with the current dietary advice that this ratio should be about 10:1 and also at odds with Simopoulos, A. P. (Biomed. Pharmacother., 56, 365-379, (2002)) and Simopoulos, A. P. (World Rev. Nutrit. Dietet., 92, 1-174 (2003)) that the ratio should be more in the region of between 3:1 and 1:1. Cordain L. et al. (Am. J. Clin. Nutrit., 71, 682-692 (2000)) suggests that in hunter-gatherer diets the ratio is 1.5:1.

Digestion of Daily Diets

The aforementioned daily diets were split into the following groups for treatment in an artificial gut to test for their effects on the gut microbiota

TABLE 7

Ingredients of diets split by groups as for treatment in an artificial gut ("UH" means unhealthy diet, "HE" means diet based on WHO guidelines, "FR" means Frasetto based diet and "PA" means Paleolithic based diet; pre-digestions were performed with (+) or without (−) bile; "*" means that PA7 and PA13 were combined into PA3 with the figures for the combination given under PA3)

| Designation | Contents | Food groups | Bile | start amount g | contribution % | per fermentation % | g |
|---|---|---|---|---|---|---|---|
| UH1 | Baked beans, ready to eat rice pudding, white bread | Starchy ingredients | − | 305 | 100 | 68.9 | 1.516 |
| UH2 | Salted butter, Cheddar cheese, milk | Fat and protein | + | 382 | 6 | 5.2 | 0.114 |
| UH9 | Milk chocolate | Milk chocolate | + | 44 | 6 | 0.6 | 0.013 |
| UH10 | Oven chips | Oven chips | + | 100 | 100 | 22.6 | 0.497 |
| UH11 | Pork Sausage | Pork Sausage | + | 200 | 6 | 2.7 | 0.060 |
| HE1 | Cheerios (cereal), multigrain bread, red kidney beans, white long grain rice | Starchy ingredients | − | 541 | 100 | 40.5 | 0.892 |
| HE2 | Grilled haddock, milk, olive oil | Fat and protein | + | 434 | 6 | 2.0 | 0.043 |
| HE3 | Banana, orange juice, peach | Fruit | − | 486 | 100 | 36.4 | 0.801 |
| HE4 | Carrots, cucumber with peel, sweet red peppers, tomatoes | Vegetables | − | 260 | 100 | 19.5 | 0.429 |
| HE10 | Oven chips | Oven chips | + | 18 | 100 | 1.3 | 0.030 |
| HE12 | Twix bar (2 sticks) | Twix bar (2 sticks) | + | 58 | 6 | 0.3 | 0.006 |
| FR1 | olive oil, salmon, prawns | Fat and protein | + | 399 | 6 | 1.6 | 0.036 |
| FR2 | melon, lemon juice, blueberries, avocado | Fruit | − | 424 | 100 | 29.0 | 0.638 |
| FR3 | spinach, tomatoes, cucumber, raw carrot, steamed broccoli, lettuce, tomatoes, red onion | Vegetables | − | 992 | 100 | 67.9 | 1.494 |
| FR4 | pork chops | Protein | + | 280 | 6 | 1.1 | 0.025 |
| FR5 | sliced almonds | Seeds | + | 72 | 6 | 0.3 | 0.007 |
| PA3* | Grapefruit, Kiwifruit, apple with skin, strawberries, sweet cherries | Fruit | − | 791 | 100 | 40.2 | 0.885 |
| PA4 | Aubergine, broccoli, carrots, celery, fresh basil, garlic, ginger root, onions, peas (frozen), Savoy cabbage, spinach, sweet yellow peppers, tomatoes, watercress, white mushrooms | Vegetables | − | 1130 | 100 | 57.4 | 1.264 |
| PA5 | Chicken breast (meat only, no skin), egg, farmed Atlantic salmon, shrimps/prawns | Protein | + | 700 | 6 | 2.1 | 0.047 |
| PA6 | Brown flaxseeds, celery seeds, hazelnuts, tahini | Seeds | + | 61 | 6 | 0.2 | 0.004 |
| PA7* | Dried blue berries with apple juice, dried figs, dried unsulphured apricots, seedless raisins | Dried fruit | | | | | |
| PA13* | Honey | Honey | | | | | |

(a) Pre-Digestion

Daily diets were separated into components of similar protein, fat or carbohydrate composition as shown in table 7 and pre-digestion performed according to Miller et al. (Am. J. Clin. Nutr., 34, 2248-2256 (1981)). To each component was added sufficient water to obtain a suspension after mixing with a hand blender, this suspension was adjusted to pH 2.0 with 6 M HCl at which point Hog pepsin was added to a final concentration of 5 mg/mL. The suspension was then incubated for 2 hours at 37 degrees centigrade after which the pH was adjusted to pH>5.0 with 6 M NaOH. Pancreatin was then added to a final concentration of 0.8 mg/mL. Bile was then added to fat based components to a final concentration of 5 mg/mL. The pH was further increased to 7.0 and maintained neutral with 1 M NaOH and 1 M HCL by means of a pH controller (Electrolab) for 2 hours at 37 degrees centigrade. Degradation products were exhaustively removed by dialysis of the resulting suspension for 26 hours against water in a dialysis tube (Spectra/Por) with a 1 kDa molecular weight cut-off (Serve Electrophoresis GmbH) at 8-12 degrees centigrade with constant removal of the permeate (water was refreshed continuously) to simulate absorption of smaller molecules through the wall of the small intestine. The retentate was freeze-dried.

(b) Batch Fermentation

An estimate of the amount of each of the retentates which should contribute to that which is then fermented were estimated from the literature and is given in table 7 under the column entitled "contribution". The relevant amounts of each retentate were accordingly combined to reconstitute the daily diet after pre-digestion. Fermentations were performed based on both equal weights of reconstituted daily diets as well as using amounts normalised on the relative contribution of each diet. Diets were assumed to be of equal caloric content prior to pre-digestion. Relative amounts of each diets used in the fermentations were calculated based on their calculated total weight after pre-digestion taking into account the relative contribution of each ingredient group.

Batch fermentations with pH control were performed in triplicate with faecal matter of two different healthy human volunteers who had not been prescribed antibiotics for at least 6 months prior to the study and had no history of any gastrointestinal disease. The faecal matter was, immediately after collection, stored at 37 degrees centigrade under anaerobic conditions. The faecal matter was diluted 10-fold in anaerobic phosphate buffered saline (PBS) (8 g NaCl, 0.2 g KCL, 1.15 g $Na_2HPO_4$, 0.2 g $KH_2PO_4$, pH=7.3) and homogenised in a stomacher for 2 minutes creating a faecal slurry.

Fermentations were performed in 300 mL water-jacketed chemostats (Soham Scientific) filled with 180 mL basal medium (per liter, 2 g peptone water (Oxoid), 2 g yeast extract (Bacto), 2 g $NaHCO_3$, 0.5 g bile salts No3 (Oxoid), 0.5 g L-cysteine, 10 mL of each of the following solutions NaCl (10 g/L; Fisher Scientific), $K_2HPO_4$ (4 g/L; Merck), $KH_2PO_4$ (4 g/L; Sigma), $MgSO_4 \cdot 7H_2O$ (1 g/L; Merck), $CaCl_2 \cdot 6H_2O$ (1 g/L; Fisher Scientific), 10 mL hemin solution (0.5 g/L; Sigma), 4 mL resazurin solution (0.25 g/L (Brocades Stheeman & Pharmacia)), 2 mL polysorbate 80, 10 μL vitamin K1). The basal medium was initially autoclaved at 121 degrees centigrade for 15 minutes and then maintained at 37 degrees centigrade and the pH maintained at pH 6.8-7.0 by means of a pH controller (Electrolab). The basal medium was continuously sparged with $O_2$-free $N_2$. The combined retentates for each of the diets from the pre-digestion step was re-suspended in 20 mL basal medium and added to the chemostat and inoculated with 20 mL of faecal slurry. The final concentration of the combined retentates for each diet was 1% w/v when diets were equalised on mass or normalised based on relative contribution with the diet with the lowest contribution set at 0.5% w/v in a total volume of 220 mL. Multiple 1 mL samples were withdrawn from the chemostat at 0, 4, 8, 19, 27, 44 hours. The samples were centrifuged for 2 minutes on a table top centrifuge at maximum speed to harvest cells were from the supernatant. Both pellets and supernatant were frozen at −20 degrees centigrade for later use.

Blank and inulin only fermentations (no pre-digestion required) were conducted with the amount of inulin matching the amount of combined retentates for each diet. Inulin was used as a positive control to confirm that fermentation was taking place DNA Isolation DNA isolation from frozen cell pellets for microbial quantification was carried out with the Stool isolation kit from Qiagen according to the manufacturer's instructions with the following modifications. 600-650 mg 0.1 mm zirconia/silica glass beads (BioSpec Products) was added to cells re-suspended in a cell lysis buffer (ASL buffer provided in kit). The suspension with beads was subsequently shaken for 45 seconds at speed setting 6 in a high-speed benchtop reciprocating device for disruption of cell membranes (Fastprep® FP120 (MP Biomedicals)). This process led to mechanical lysis of the cells. The obtained suspension was incubated for 5 minutes at 95 degrees centigrade and the obtained DNA stored at −20 degrees centigrade until further use.

Microbial Quantification by qPCR

Primers (Applied Biosystems or Invitrogen) for each of the seven targets, reference DNA, target organisms, genome weights and polymerase chain reaction (PCR) conditions are listed in Table 8. A computer readable Sequence Listing of these primers were submitted as an ASCII text file identified as 13698.685 2 ST25.txt, which text file is incorporated herein by reference. The text file is 5 KB in size and was created on Jan. 22, 2013. Quantitative PCR reactions and subsequent dissociation analysis were performed on an Applied Biosystems 7500 real time PCR machine using the 7500 Real-Time PCR System Sequence Detection Software, Version 1.3.1 (Applied Biosystems). Assays were performed in 25 IJL volumes containing 12.5 IJL POWER SYBR Green I PCR Master Mix, 5 forward and reverse primers and 2.5 IJL of a 10 fold dilution of the extracted DNA.

TABLE 8

| PCR conditions and reference strains used for bacterial enumeration | | | | |
|---|---|---|---|---|
| PCR target (Amplicon size, reference DNA, size of reference DNA) | Annealing** | primers (nM) | sequences (5'-->3') | Primer SEQ ID |
| Total bacteria (466, F. prausznitzii ATCC 27766 16S DNA PCR product*, 1540 bp) | 55 | F_eub (100) | TCCTACGGGAGGCAGCAGT | 1 |
| | | R_eub (100) | GGACTACCAGGGTATCTAATCCTGTT | 2 |

TABLE 8-continued

PCR conditions and reference strains used for bacterial enumeration

| PCR target (Amplicon size, reference DNA, size of reference DNA) | Annealing** | primers (nM) | sequences (5'-->3') | Primer SEQ ID |
|---|---|---|---|---|
| Bifidobacterium (550, B. longum ATCC15707, 3 Mb) | 55/60 | g-Bifid-F (100) | CTCCTGGAAACGGGTGG | 3 |
|  |  | g-Bifid-R (100) | GGTGTTCTTCCCATATCT ACA | 4 |
| Bacteroides fragilis group (495, B. eggerthi ATCC 27754, 1.6 Mb) | 55 | g-Bfra-F (100) | ATAGCCTTTCGAAAGRA AGAT | 5 |
|  |  | g-Bfra-R (100) | CCAGTATCAACTGCAAT TTTA | 6 |
| Clostridium coccoides group (440, R. productus ATCC 27340, 4 Mb) | 55 | g-Ccoc-F (100) | AAATGACGGTACCTGAC TAA | 7 |
|  |  | g-Ccoc-R (100) | CTTTGAGTTTCATTCTTG CGAA | 8 |
| Clostridium leptum group (239, F. prausznitzii ATCC 27766 16S DNA PCR product*, 1540 bp) | 55 | sp-Clept-F (100) | GCACAAGCAGTGGAGT | 9 |
|  |  | sp-Clept-R (100) | CTTCCTCCGTTTTGTCAA | 10 |
| F prausznitzii (199, F. prausznitzii ATCC 27766 16S DNA PCR product*, 1540 bp) | 62/64 | Fpr1 (100) | AGATGGCCTCGCGTCCG A | 11 |
|  |  | Rpr1 (100) | CCGAAGACCTTCTTCCT CC | 12 |
| Lactobacillus (340, L. reuteri ATCC 55730, 2 Mb) | 58/63 | Lac1 (800) | AGCAGTAGGGAATCTTC CA | 13 |
|  |  | Lab-0677 (800) | CACCGCTACACATGGAG | 14 |
| B. fragilis (243, Bacteroides fragilis CMCC 2151, 1.6 Mb) | 60 | BaFRA-F (1000) | TGATTCCGCATGGTTTC ATT | 17 |
|  |  | BaFRA-R (1000) | CGACCCATAGAGCCTTC ATC | 18 |
| E. coli O157:H7 (63, E. coli O157:H7 CMCC 3571, 2.5 Mb) | 60 | EcO157F (200) | TCGAGCGGACCATGATC A | 19 |
|  |  | EcO157R (200) | GGCGGCGTCTGAGATAA CA | 20 |

*F. prausnitzii is difficult to cultivate therefore the F. prausnitzii 16S rDNA is amplified with primers TPU1 (AGAGTTTGATCMTGGCTCAG) (primer Seq. Id. 15) and RTU8 (AAGGAGGTGATCCANCCRCA) (primer Seq. Id. 16) to serve as a reference
**Each amplification consisted of a hold at 10'95° C. followed by 40 cycles of 15" at 95° C., variable annealing each time for 20" and extension between 60-72° C. each time for 1 min.

For quantitative analysis the threshold cycle (Ct) of each sample was compared to a standard curve made from serial DNA dilutions of chromosomal DNA of the corresponding reference strain. The number of cells equivalent to one μL of reference DNA is calculated by dividing the DNA concentration by the genome weight. The genome weight in turn is calculated by multiplying the base pair weight (607.4 g/mol) with the relevant genome size in by and divided by the Avogadro number (6.02E+23). Calculation is done with a copy number of the reference material of 1 indicating that one target genome or 16S recombinant DNA (rDNA) molecule is representative for one bacterial cell. Results were expressed as copy numbers/mL taking into account the dilution steps in the DNA isolation method.

FIGS. 1a and 1b show that there is a significant decrease of F. prausznitzii in the unhealthy diet whilst Faecalibacterium prausznitzii was supported for the diet based on WHO guidelines and the Paleolithic based diet. Faecalibacterium prausznitzii is a bacterium which is thought to have anti-inflammatory properties and absent or less dominant in patient suffering from inflammatory bowel disease.

FIGS. 2a to 2c and FIGS. 3a to 3c, the latter set of figures for diets normalised on the relative contribution of each diet, show that whilst there is, as expected some variation in the numbers of microbes from volunteer to volunteer, the Paleolithic based diet generally shows higher total levels of microbes.

Semi-quantitative analysis of the levels of bacteria using HITChip analysis

Human intestinal tract chip (HITChip) analysis was performed by GI-Health B.V. according to Rajilic-Stojanovic, M. (Diversity of the human gastrointestinal microbita novel perspectives from high throughput analyses (2007)). Briefly the 16S rDNA was amplified using the primers T7prom-Bact-27-for (5'-TGA ATT GTA ATA CGA CTC ACT ATA GGG GTT TGA TCC TGG CTC AG-3') (primer Seq. Id. 17) and Uni-1492-rev (5'-CGG CTA CCT TGT TAC GAC-3') (primer Seq. Id. 18) (GI-Health B.V.). The PCR product was purified and quantified, followed by in vitro transcription of the T7-promoter, introduced via the T7prom-Bact-27-for primer, using the Riboprobe System (Promega). Generated RNA, labelled with amino-allyl-modified nucleotides, was treated with deoxyribonuclease (DNase), purified and coupled to either Cy3 or Cy5 (both reactive water-soluble fluorescent dyes of the cyanine dye family) with CyDye using the Post-Labeling Reactive Dye (Amersham Biosciences). Custom microarrays were synthesised by Agilent Technologies (Agilent Technologies). Each array was hybridised with two samples, labelled with Cy3 and Cy5 respectively and measured. Target mixtures were created by fragmenting labelled RNA mixtures using Ambion fragmentation reagent (Ambion) for 20 minutes at 70 degrees centigrade. Arrays were hybridised overnight, washed and dried. Data was extracted from microarray images using Agilent extraction software and normalised.

The results are illustrated in FIG. 2 which show changes in the log intensity values over time (hours) for *Aeromonas* sp. and *Bacteroides fragilis* generated by HITchip analysis for the unhealthy diet ("unhealthy"), the diet based on WHO guidelines ("healthy") and the Paleolithic based diet ("Paleolithic"). HITchip and qPCR results showed that *Bacteroides* was increased in the fermentation of the Palaeolithic based diet compared to the other diets (taking into account that total fermentation was less for the Palaeolithic based diet (see table 9) so even though less material was fermented comparable amounts of *bacteroides* were seen for the Palaeolithic based diet suggesting that if fermentable levels were equal the number of *Bacteroides* for the Palaeolithic based diet would be higher). Similarly HITchip analysis also showed an increase in *Aeromonas* sp. for the fermentation of the Paleolithic based diet. These results indicate that the Palaeolithic based diet leads to an increased robustness against bacterial infections causing diarrhoea more specifically by *Aeromonas* sp and toxigenic *Baceteroides fragilis*. Furthermore both increases in bacterial populations could be linked to an increased resistance to infectious diseases in particular to infections of toxigenic members of *Aeromonas* and *Bacteroides* sp. The rationale behind this is that an increase in non-toxigenic bacteria of the same species stimulates the immune system to recognize these type of bacteria and secondly the increased level of non-pathogenic bacteria occupying the same niche are a better barrier to invasion by other pathogenic bacteria.

NMR Analysis

The supernatants from the fermentations were thawed and centrifuged for 5 minutes at 21912×g at 8 degrees centigrade. NMR samples were prepared by adding 50 µL deuterium oxide ($D_2O$) containing 10 mM deuterated sodium trimethylsilyl propionate (d-TSP) to 450 µL supernatant. $D_2O$ and d-TSP serve as field frequency lock and chemical shift references respectively. One-dimensional (1D) high-resolution $^1H$ NMR spectra were acquired on a Bruker Avance 600 NMR spectrometer operating at a proton NMR frequency of 600.13 MHz and at a temperature of 300 K. A 5 mm TXI probe and a sample changer for sample delivery were used. A Noesypresat pulse sequence with 32 k data points and 64 scans over 8993 Hz was used. Water suppression was achieved during the relaxation delay (3 s) and the mixing time (150 ms). The spectra were manually corrected for phase and baseline distortions using Topspin 1.3 software (Bruker Analytik, Rheinstetten, Germany). An exponential window function with a line-broadening factor of 0.3 Hz was applied to the free induction decay (FID) prior to Fourier transformation. The spectra were referenced to TSP. Metabolites were identified using a database including reference spectra of metabolites at different pH values (biorefcode-2-0-0 implemented in Amix 3.7.3. (Bruker Biospin GmbH)). The metabolites were quantified using the software ChenomX NMR Suite 5.1. (ChenomX Inc.).

TABLE 9

Relative proportions (%) of short chain fatty acids (SCFA) versus fermentation time (hours), in particular propionic, butyric, acetic and lactic acids in the no food diet ("bl"), the unhealthy diet ("uh"), the diet based on WHO guidelines ("he"), the Paleolithic based diet ("pa") and the diet based on inulin ("in") ("P/A" propionate:acetate ratio; total SCFA given in mg).

| | | SCFA ratio (%) and total amounts (mM) | | | | | | | | | | | |
|---|---|---|---|---|---|---|---|---|---|---|---|---|---|
| | | Batch fermentation volunteer 1 | | | | | | Batch fermentation volunteer 2 | | | | | |
| substrate | Time (h) | propionic acid | butyric acid | acetic acid | lactic acid | total SCFA | P/A | propionic acid | butyric acid | acetic acid | lactic acid | total SCFA | P/A |
| Bl | 0 | 15% | 28% | 28% | 30% | 8.88 | 0.52 | 13% | 27% | 24% | 36% | 11.29 | 0.53 |
| Bl | 4 | 19% | 25% | 43% | 13% | 16.03 | 0.45 | 20% | 26% | 40% | 14% | 17.93 | 0.49 |
| Bl | 8 | 20% | 26% | 47% | 7% | 23.12 | 0.42 | 24% | 25% | 41% | 10% | 25.92 | 0.58 |
| Bl | 19 | 21% | 27% | 48% | 4% | 26.72 | 0.44 | 25% | 26% | 41% | 8% | 27.62 | 0.61 |
| Bl | 27 | 21% | 28% | 47% | 3% | 26.76 | 0.45 | 26% | 27% | 40% | 7% | 28.19 | 0.65 |
| Bl | 44 | 22% | 28% | 46% | 3% | 26.98 | 0.47 | 27% | 28% | 41% | 4% | 30.59 | 0.66 |
| Uh | 0 | 12% | 29% | 26% | 32% | 12.02 | 0.48 | 11% | 29% | 23% | 37% | 14.82 | 0.45 |
| Uh | 4 | 12% | 14% | 50% | 23% | 43.35 | 0.20 | 14% | 22% | 51% | 13% | 49.90 | 0.32 |
| Uh | 8 | 19% | 16% | 63% | 3% | 59.07 | 0.26 | 21% | 25% | 50% | 3% | 65.07 | 0.38 |
| Uh | 19 | 19% | 16% | 63% | 1% | 72.94 | 0.26 | 22% | 26% | 50% | 2% | 75.07 | 0.32 |
| Uh | 27 | 20% | 17% | 63% | 1% | 72.35 | 0.26 | 22% | 26% | 50% | 2% | 77.20 | 0.33 |
| Uh | 44 | 20% | 17% | 62% | 1% | 75.79 | 0.27 | 23% | 27% | 49% | 2% | 81.83 | 0.34 |
| He | 0 | 14% | 28% | 30% | 28% | 10.04 | 0.52 | 12% | 28% | 26% | 34% | 11.70 | 0.50 |
| He | 4 | 11% | 14% | 55% | 21% | 41.04 | 0.19 | 16% | 21% | 50% | 13% | 42.64 | 0.25 |
| He | 8 | 17% | 16% | 65% | 2% | 60.73 | 0.27 | 20% | 25% | 53% | 2% | 56.10 | 0.25 |
| He | 19 | 16% | 19% | 64% | 1% | 73.42 | 0.28 | 17% | 26% | 54% | 3% | 73.52 | 0.25 |
| He | 27 | 16% | 20% | 63% | 1% | 76.97 | 0.29 | 18% | 26% | 54% | 3% | 73.93 | 0.25 |
| He | 44 | 16% | 21% | 61% | 1% | 76.96 | 0.30 | 18% | 27% | 53% | 2% | 77.38 | 0.26 |
| Pa | 0 | 15% | 28% | 31% | 26% | 10.04 | 0.47 | 14% | 28% | 27% | 31% | 9.39 | 0.52 |
| Pa | 4 | 14% | 17% | 55% | 15% | 33.71 | 0.26 | 19% | 25% | 51% | 4% | 31.21 | 0.38 |
| Pa | 8 | 18% | 18% | 61% | 2% | 47.77 | 0.30 | 23% | 23% | 52% | 2% | 46.43 | 0.43 |
| Pa | 19 | 18% | 19% | 60% | 2% | 53.36 | 0.31 | 21% | 24% | 52% | 2% | 51.95 | 0.40 |
| Pa | 27 | 19% | 20% | 60% | 1% | 57.17 | 0.31 | 21% | 24% | 52% | 2% | 53.47 | 0.41 |
| Pa | 44 | 19% | 22% | 58% | 2% | 57.80 | 0.32 | 22% | 25% | 51% | 2% | 56.18 | 0.43 |

TABLE 9-continued

Relative proportions (%) of short chain fatty acids (SCFA) versus fermentation time (hours), in particular propionic, butyric, acetic and lactic acids in the no food diet ("bl"), the unhealthy diet ("uh"), the diet based on WHO guidelines ("he"), the Paleolithic based diet ("pa") and the diet based on inulin ("in") ("P/A" propionate:acetate ratio; total SCFA given in mg).

| | | SCFA ratio (%) and total amounts (mM) | | | | | | | | | | | |
|---|---|---|---|---|---|---|---|---|---|---|---|---|---|
| | | Batch fermentation volunteer 1 | | | | | | Batch fermentation volunteer 2 | | | | | |
| substrate | Time (h) | propionic acid | butyric acid | acetic acid | lactic acid | total SCFA | P/A | propionic acid | butyric acid | acetic acid | lactic acid | total SCFA | P/A |
| In | 0 | 14% | 27% | 27% | 32% | 8.80 | 0.47 | 13% | 27% | 25% | 35% | 10.38 | 0.47 |
| In | 4 | 10% | 17% | 53% | 20% | 34.52 | 0.24 | 12% | 21% | 50% | 16% | 47.73 | 0.27 |
| In | 8 | 18% | 16% | 64% | 2% | 69.79 | 0.31 | 14% | 27% | 56% | 2% | 68.86 | 0.42 |
| In | 19 | 18% | 17% | 64% | 1% | 81.75 | 0.31 | 14% | 26% | 57% | 3% | 79.38 | 0.45 |
| In | 27 | 18% | 18% | 63% | 1% | 80.36 | 0.31 | 14% | 27% | 57% | 3% | 81.36 | 0.45 |
| In | 44 | 18% | 19% | 62% | 1% | 94.97 | 0.32 | 14% | 27% | 56% | 3% | 86.15 | 0.47 |

Some results are summarised in table 9 which show relative proportions of short chain fatty acids (SOFA) versus fermentation time, in particular propionic, butyric, acetic and lactic acids in the no food diet ("bl"), the unhealthy diet ("uh"), the diet based on WHO guidelines ("he"), the Paleolithic based diet ("pa") and the diet based on inulin ("in"). It is clear that the Palaeolithic based diet showed the highest propionate:acetate ratio (P/A). This suggests that the Palaeolithic based diet may lead to improved cardiovascular health.

The results of a second round of fermentations is summarised in table 10 where it can be seen that the propionate:acetate ratio (P/A) is, generally speaking, higher for the Paleolithic based diet than for the diet based on WHO guidelines or that based on the Frassetto paper and therefore supports the data in table 9.

TABLE 10

Short chain fatty acids (SCFA) (mM) versus fermentation time (hours), in particular propionic, butyric, acetic and lactic acids in the no food diet ("bl"), the unhealthy diet ("uh"), the diet based on WHO guidelines ("he"), the Paleolithic based diet ("pa"), the Frassetto paper based diet ("fr") and the diet based on inulin ("in") ("P/A" propionate:acetate ratio; total SCFA given in mg). Fermentations with diets based on equal weights are indicated by "1" (ie "uh1", "he1", "fr1" and "pa1") whilst fermentations with diets normalised on their relative contribution are indicated by "2" (ie "uh2", "he2", "fr2" and "pa2"). "NA" indicates number not available.

| | | SCFA ratio | | | | | | | | |
|---|---|---|---|---|---|---|---|---|---|---|
| | | Batch fermentation volunteer 1 | | | | | | Batch fermentation volunteer 2 | | |
| substrate | Time (h) | propionic acid | butyric acid | acetic acid | lactic acid | total SCFA | P/A | propionic acid | butyric acid | acetic acid |
| Bl | 0 | 1.0 | 3.9 | 3.7 | 6.3 | 14.9 | 0.26 | 0.7 | 3.4 | 2.5 |
| Bl | 46 | 8.5 | 8.5 | 19.7 | 2.9 | 39.5 | 0.43 | 10.1 | 10.7 | 19.9 |
| Pa1 | 0 | 1.0 | 4.6 | 4.4 | 4.9 | 14.9 | 0.22 | 0.7 | 3.4 | 3.3 |
| Pa1 | 46 | 20.9 | 12.8 | 50.9 | 1.0 | 85.5 | 0.41 | 24.6 | 25.7 | 36.1 |
| Fr1 | 0 | 1.0 | 5.6 | 4.6 | 5.8 | 17.0 | 0.23 | 0.8 | 4.4 | 3.3 |
| Fr1 | 46 | 19.6 | 11.2 | 46.2 | 1.6 | 78.7 | 0.42 | 28.3 | 27.2 | 44.4 |
| Uh | 0 | 1.0 | 5.1 | 3.8 | 6.6 | 16.4 | 0.27 | 0.8 | 3.9 | 2.8 |
| Uh | 46 | 19.2 | 10.5 | 35.5 | 2.8 | 68.0 | 0.54 | 20.3 | 21.8 | 27.7 |
| He | 0 | 1.0 | 3.3 | 5.4 | 2.9 | 12.6 | 0.19 | 0.6 | 3.4 | 3.2 |
| He | 46 | 28.2 | 27.0 | 101.7 | 1.2 | 158.1 | 0.28 | 19.0 | 12.7 | 95.6 |
| Pa2 | 0 | 1.1 | 5.4 | 5.5 | 4.8 | 16.8 | 0.19 | 0.7 | 4.5 | 4.4 |
| Pa2 | 46 | 34.8 | 13.2 | 119.6 | 0.7 | 168.3 | 0.29 | 30.7 | 24.5 | 82.6 |
| Fr2 | 0 | 1.0 | 5.2 | 4.6 | 5.0 | 15.9 | 0.21 | 0.7 | 4.7 | 4.0 |
| Fr2 | 46 | 26.2 | 10.6 | 59.4 | 0.9 | 97.1 | 0.44 | 38.1 | 29.0 | 67.2 |
| In | 0 | 0.9 | 3.9 | 3.5 | 6.1 | 14.4 | 0.26 | traces | 2.9 | 2.1 |
| In | 46 | 26.0 | 16.7 | 80.9 | 1.8 | 125.4 | 0.32 | 15.4 | 24.7 | 42.9 |

| | | SCFA ratio | | | | | | | |
|---|---|---|---|---|---|---|---|---|---|
| | | Batch fermentation volunteer 2 | | | Batch fermentation volunteer 3 | | | | |
| substrate | | lactic acid | total SCFA | P/A | propionic acid | butyric acid | acetic acid | lactic acid | total SCFA | P/A |
| Bl | | 5.8 | 12.5 | 0.28 | traces | 3.1 | 2.1 | 5.1 | 10.4 | NA |
| Bl | | 3.1 | 43.8 | 0.51 | 6.1 | 8.2 | 13.8 | 2.5 | 30.5 | 0.44 |
| Pa1 | | 4.2 | 11.5 | 0.21 | 0.6 | 2.9 | 3.0 | 3.3 | 9.8 | 0.19 |

TABLE 10-continued

Short chain fatty acids (SCFA) (mM) versus fermentation time (hours), in particular propionic, butyric, acetic and lactic acids in the no food diet ("bl"), the unhealthy diet ("uh"), the diet based on WHO guidelines ("he"), the Paleolithic based diet ("pa"), the Frassetto paper based diet ("fr") and the diet based on inulin ("in") ("P/A" propionate:acetate ratio; total SCFA given in mg). Fermentations with diets based on equal weights are indicated by "1" (ie "uh1", "he1", "fr1" and "pa1") whilst fermentations with diets normalised on their relative contribution are indicated by "2" (ie "uh2", "he2", "fr2" and "pa2"). "NA" indicates number not available.

| | | | | | | | | | |
|---|---|---|---|---|---|---|---|---|---|
| Pa1 | 1.6 | 88.1 | 0.68 | 18.1 | 11.2 | 46.5 | 1.0 | 76.9 | 0.39 |
| Fr1 | 5.1 | 13.6 | 0.24 | 0.6 | 3.5 | 3.4 | 3.6 | 11.2 | 0.19 |
| Fr1 | 1.7 | 101.6 | 0.64 | 13.7 | 10.8 | 36.9 | 2.6 | 64.0 | 0.37 |
| Uh | 6.1 | 13.5 | 0.27 | 0.6 | 3.6 | 2.6 | 5.2 | 12.0 | 0.24 |
| Uh | 2.6 | 72.4 | 0.73 | 25.3 | 13.8 | 58.0 | 1.6 | 98.7 | 0.44 |
| He | 3.5 | 10.6 | 0.20 | 0.5 | 2.5 | 2.6 | 2.2 | 7.8 | 0.19 |
| He | 1.4 | 128.7 | 0.20 | 24.7 | 13.7 | 85.7 | 0.9 | 125.1 | 0.29 |
| Pa2 | 4.0 | 13.6 | 0.15 | 0.8 | 4.7 | 4.8 | 3.5 | 13.8 | 0.17 |
| Pa2 | 1.2 | 139.0 | 0.37 | 36.6 | 9.7 | 88.6 | 0.5 | 135.5 | 0.41 |
| Fr2 | 4.5 | 14.0 | 0.18 | 0.7 | 4.6 | 3.9 | 4.1 | 13.4 | 0.18 |
| Fr2 | 2.0 | 136.3 | 0.57 | 24.8 | 8.2 | 61.5 | 1.2 | 95.5 | 0.40 |
| In | 5.3 | 10.4 | NA | traces | 2.6 | 2.0 | 4.4 | 9.0 | NA |
| In | 2.1 | 85.1 | 0.36 | 20.8 | 15.9 | 47.7 | 1.4 | 85.8 | 0.44 |

The invention claimed is:

1. A method,
wherein the method treats inflammatory bowel disease in a subject in need thereof,
wherein the method comprises administering to the subject an effective amount of a daily diet comprising:
(a) 1750 to 2750 kilocalories (7350 to 11550 kilo-Joules);
(b) have more than 1650, mg gallic acid equivalents of poly phenols;
(c) have more than 40 g fibre;
(d) have more than 130 g protein;
(e) have 2 g starch or less; and
(f) have 2.5 g of lactose or less;
wherein the amount of *Faecacilbacterium prausznitzii* present in the fecal matter of the subject, determined by the copy number of 16S DNA/ml, is greater following administration of the effective amount of the daily diet compared to the amount of *Faecacilbacterium prausznitzii* present in the fecal matter of the subject prior to the administration of the effective amount of the daily diet,
wherein the amount of *Faecacilbacterium prausznitzii* present in the fecal matter of the subject is determined in a fecal sample taken from the subject;
wherein the *Faecacilbacterium prausznitzii* has anti-inflammatory properties.

2. The method of claim 1, wherein the compositions comprise a daily diet of more than 1700 mg gallic acid equivalents of polyphenols.

3. The method according to claim 1, wherein the plurality of compositions comprises a daily diet of at least 110 distinct polyphenols.

4. The method according to claim 1, wherein the plurality of compositions comprises a daily diet of at least 0.1 mg of at least one anthocyanidin.

* * * * *